United States Patent
Hunt et al.

(10) Patent No.: US 7,749,769 B2
(45) Date of Patent: *Jul. 6, 2010

(54) SIMULTANEOUS SEQUENCE ANALYSIS OF AMINO- AND CARBOXY-TERMINI

(75) Inventors: Donald F Hunt, Charlottesville, VA (US); Joshua J. Coon, Madison, WI (US); John Edward Philip Syka, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 485 days.

This patent is subject to a terminal disclaimer.

(21) Appl. No.: 11/664,661

(22) PCT Filed: Oct. 7, 2005

(86) PCT No.: PCT/US2005/036337

§ 371 (c)(1),
(2), (4) Date: Apr. 4, 2007

(87) PCT Pub. No.: WO2006/042187

PCT Pub. Date: Apr. 20, 2006

(65) Prior Publication Data

US 2008/0044915 A1   Feb. 21, 2008

Related U.S. Application Data

(60) Provisional application No. 60/617,125, filed on Oct. 8, 2004.

(51) Int. Cl.
*G01N 24/00* (2006.01)
*H01J 49/00* (2006.01)

(52) U.S. Cl. .................. 436/173; 436/181; 250/290
(58) Field of Classification Search .................. None
See application file for complete search history.

(56) References Cited

U.S. PATENT DOCUMENTS 7,534,622 B2 *   5/2009   Hunt et al. .................. 436/173

(Continued)

FOREIGN PATENT DOCUMENTS

| EP | 0 409 362 A2 | 1/1991 |
| WO | WO2005/090978 | 9/2005 |

OTHER PUBLICATIONS

McLuckey et al, (Ion/Ion Chemistry of High-Mass Multiply Charged Ions, Mass Spectrometry Reviews, vol. 17, pp. 369-407 (1998)).*

(Continued)

*Primary Examiner*—Krishnan S Menon
*Assistant Examiner*—Rebecca Fritchman
(74) *Attorney, Agent, or Firm*—Barnes & Thornburg LLP

(57) ABSTRACT

The present invention relates to a new method for identifying polypeptides by deducing the amino acid sequence of the carboxy and amino termini by a mass spectrometer analysis. The method comprises the steps of dissociating highly charged peptide precursor ions (e.g., z>4) using electron transfer dissociation inducing anions followed by removal of those reagents and introduction of a second, proton transfer inducing anion type. The second PTR reaction duration is adjusted to convert the ETD products to primarily the +1 charge-state to reduce the highly charged c and z-type fragments, producing an m/z spectrum containing a series of c and z-type fragment ions that are easily interpreted to reveal the sequence of the amino and carboxy terminus, respectively.

23 Claims, 14 Drawing Sheets

U.S. PATENT DOCUMENTS

2002/0092980 A1 7/2002 Park
2002/0166958 A1 11/2002 Afeyan et al.

OTHER PUBLICATIONS

Coon, Joshua J. et al.: "Protein Identification Using Sequential Ion/Ion Reactions And Tandem Mass Spectrometry" Proceedings of the National Academy of Sciences of U.S.A. , vol. 102, No. 27, Jul. 27, 2005, pp. 9463-9468, XP002385858.

Reid, Gavin E. et al.: "Tandem Mass Spectrometry Of Ribonuclease A and B:N-Linked Glycosylation Site Analysis Of Whole Protein Ions" Analytical Chemistry , vol. 74, No. 3, Feb. 1, 2002, pp. 577-583, XP002385857.

Syka, John, Edward, Philip et al.: "Peptide And Protein Sequence Analysis By Electron Transfer Dissociation Mass Spectrometry" Proceedings of the National Academy of Sciences of U.S.A. , vol. 101, No. 26, Jun. 29, 2004, pp. 9528-9533, XP009051646.

McLafferty at al., "Electron Capture Dissociation of Multiply Charged Protein Cations. A Nonergodic Process", *J. Am. Chem. Soc.*, vol. 120, 1998, pp. 3265-3266.

Aebersold, Ruedi et al.; "Mass Spectrometry in Proteomics," Chem. Rev, vol. 101, No. 2, Feb. 2001, pp. 269-295.

Coon, Joshua J. et al., "Electron Transfer Dissociation of Peptide Anions," American Society for Mass Spectrometry, vol. 16, Nr. 6, Jun. 2005, pp. 880-882.

Douglas, et al., "Linear Ion Traps in Mass Spectrometry", 2005, *Mass Spectrometry Reviews*, No. 24, pp. 1-29.

Ficarro, et al., "Phosphoproteome Analysis by Mass Spectrometry and its Application to *Saccharomyces cerevisiae*", *J. Am. Chem. Soc.*, vol. 20, 2002, pp. 301-305.

Herron, et al., "Gas-Phase Electron Transfer Reactions from Multiply-Charged Anions to Rare Gas Cations", *J. Am. Chem. Soc.*, vol. 117, 1995, pp. 11555-11562.

Gunawardena, et al., "Electron Transfer Versus Proton Transfer in Gas-Phase Ion/Ion Reactions of Polyprotonated Peptides", *American Chem. Soc.*, vol. 127, 2005, pp. 12627-12639.

Loo, et al., "Proton Transfer Reaction Studies of Multiply Charge Proteins in a High Mass-to-Charge Ratio Quadrupole Mass Spectrometry", *J. Am. Soc. Mass Spectrometry*, vol. 5, 1994, pp. 1064-1071.

Martin, et al., "Subfemtomole MS and MS/MS Peptide Sequence Analysis Using Nano-IIPLC Micro-ESI Fourier Transform Ion Cyclotron Resonance Mass Spectrometry", *Anal. Chem.*, vol. 72, 2000, pp. 4266-4274.

McLuckey, et al., "Ion/Ion Proton-Transfer Kinetics: Implications for Analysis of Ions Derived from Electrospray of Protein Mixtures", *Anal. Chem.*, vol. 70, 1998, pp. 1198-1202.

Stephenson, et al., "Anion Effects on Storage and Resonance Ejection of High Mass-to-Charge Cations in Quadrupole Ion Trap Mass Spectrometry", *Anal. Science*, vol. 69, 1997, pp. 3760-3766.

Stephenson, et al., "Adaptation of the Paul Trap for Study of the Reaction of Multiply Charged Cations with Singly Charged Ions", *International Jouranl of Mass Spectrometry and Ion Process*, vol. 162, 1997, pp. 89-106.

Stephenson, et al., "Ion-Ion Proton Transfer Reactions of Bio-Ions Involving Noncovalent Interactions: Holomyoglobin", *J. Am. Soc. Mass Spectrometry*, vol. 8, 1997, pp. 637-644.

Stephenson, et al., "Simplification of Product Ion Spectra Derived from Multiply Charged Ions via Ion/Ion Chemistry", *Anal. Chem.*, vol. 70, 1998, pp. 3533-3544.

Wells, et al., "Dueling" ESI: Instrumentation to Study Ion/Ion Reactions of Electrospray-Generated Cations and Anions, *American Society of Mass Spectrometry*, vol. 13, 2002, pp. 614-622.

Amunugama, R., et al., "Whole Protein Dissociation in a Quadrupole Ion Trap: Identification of an a Priori Unknown Modified Protein", Feb. 1, 2004, *Analytical Chemistry*, vol. 76, No. 3, pp. 720-727.

Coon, Joshua J., et al., "Anion Dependence in the Partitioning Between Proton and Electron Transfer in lon/Ion Reactions", Jun. 19, 2004, *International Journal of Mass Spectrometry*, No. 236, pp. 33-42.

Creighton, T. E., "Proteins—Structure And Molecular Properties", 2nd Ed., 1993, *W. H. Freeman and Company*, New York.

Dryhurst, Deanna, et al., "New Twists on H2A.Z: A Histone Variant with a Controversial Structural and Functional Past", 2004, *Biochem. Cell Biology*, vol. 82, pp. 490-497.

Eng, Jimmy K., et al., "An Approach to Correlate Tandem Mass Spectral Data of Peptides with Amino Acid Sequences in a Protein Database", Jun. 29, 1994, *American Society for Mass Spectrometry*, No. 5, pp. 976-989.

Geer, Lewis Y., et al., "Open Mass Spectrometry Search Algorithm", 2004, *Journal of Proteome Research*, vol. 3, No. 5. pp. 958-964.

Hogan. Jason M., et al.. "Charge State Dependent Collision-Induced Dissociation of Native and Reduced Porcine Elastase", Mar. 3, 2003, *Journal of Mass Spectrometry*, No. 38, pp. 245-256.

Hunt, Donald F., et al.. "Pulsed Positive Negative Ion Chemical Ionization Mass Spectrometry". Dec. 1976. *Analytical Chemistry*, vol. 48, No. 14, pp. 2098-2104.

Hunt, Donald F., et al., "Electron Capture Negative Ion Chemical Ionization Mass Spectrometry", Nov. 1978, *Analytical Chemistry*, vol. 50, No. 13, pp. 1781-1784.

Johnson, B. Connor, "Posttranslational Covalent Modifications of Proteins", 1893, *Academic Press*, New York, pp. 1-17.

Lugar, Karolin, et al. "Crystal Structure of the Nucleosome Core Particle at 2.8 A Resolution", Sep. 18, 1997, *Nature*, vol. 389, pp. 251-260.

McLuckey, Scott A., et al., "Ion/Ion Chemistry of High-Mass Multiply Charged Ions", 1998, *Mass Spectrometry Reviews* No. 17, pp. 369-407.

Rattan, Suresh. I. S., et al., "Protein Synthesis, Posttranslational Modifications, and Aging", 1992, *Annals New York Academy of Sciences*, No. 663, pp. 48-62.

Reid, Gavin E., et al., "Gas-Phase Concentration, Purification, and Identification of Whole Proteins from Complex Mixtures", Feb. 18, 2002, *American Chemical Society*, vol. 124, No. 25, pp. 7353-7362.

Reid, Gavin E., et al., "Top Down Protein Characterization Via Tandem Mass Spectrometry", Jul. 3, 2002, *Journal of Mass Spectrometry*, No. 37, pp. 663-675.

Schwartz, Jae C., et al., "A Two-Dimensional Quadrupole Ion Trap Mass Spectrometer", Mar. 11, 2002, *American Society for Mass Spectrometry*, No. 13, pp. 659-669.

Seifter, Sam, et al., "Analysis for Protein Modifications and Nonprotein Cofactors", 1990, *Methods in Enzymology*, vol. 182, pp. 626-646.

Syka, John E. P., et al., "Novel Linear Quadrupole Ion Trap/FT Mass Spectrometer: Performance Characterization and Use in the Comparative Analysis of Histone H3 Post-Translational Modifications", 2004, *Journal of Proteome Research*, vol. 3, No. 3, pp. 621-626.

Syka, John E. P., et al., "Peptide and Protein Sequence Analysis by Electron Transfer Dissociation Mass Spectrometry", Jun. 29, 2004, *PNAS*, vol. 101, No. 26, pp. 9528-9533.

Stephenson, James L., et al., "Ion/Ion Proton Transfer Reactions for Protein Mixture Analysis", Nov. 15, 1996, *Analytical Chemistry*, vol. 68, No. 22, pp. 4026-4032.

Wells, J. Mitchell, et al., "Formation and Characterization of Protein-Protein Complexes in Vacuo", 2003, *Journal American Chem. Society*, vol. 125, No. 24, pp. 7238-7249.

Zubarev, Roman, A., et al., "Electron Capture Dissociation of Multiply Charged Protein Cations. A Nonergodic Process", 1998, *Journal American Chemical Society*, vol. 120, No. 13, pp. 3265-3266.

* cited by examiner

NICI Source Gas Inlet Connections Used For The Initial ETD Experiments

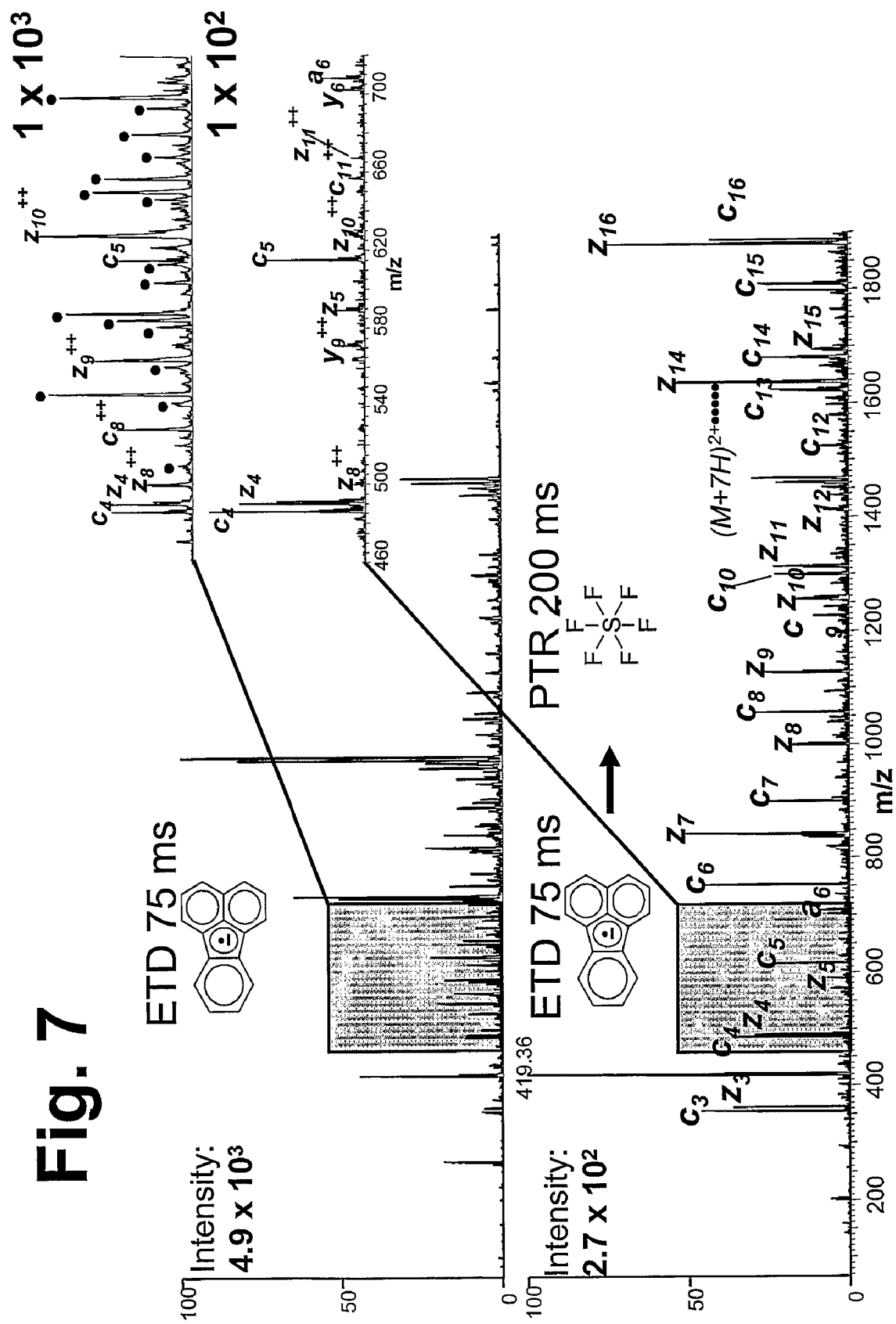

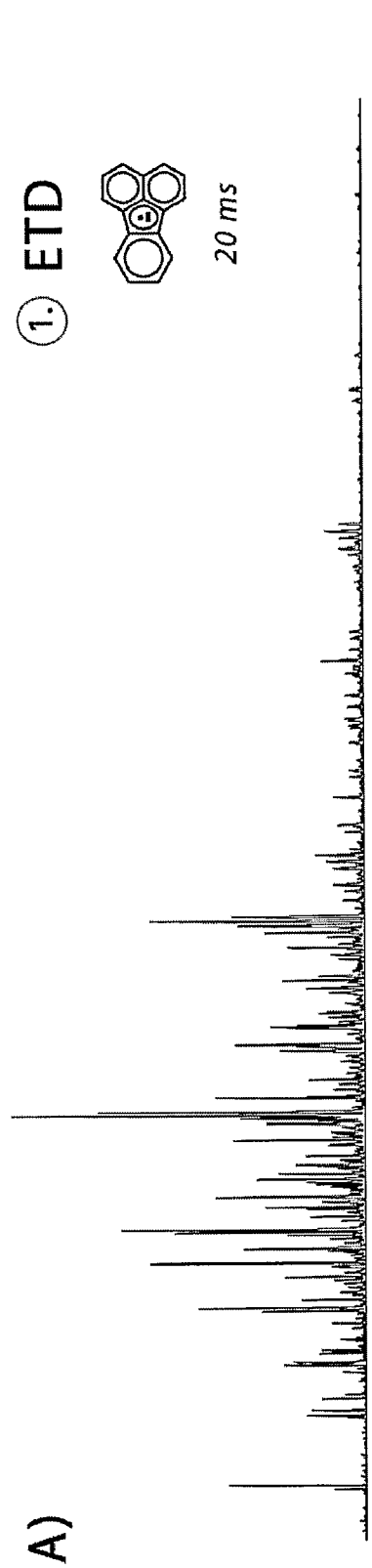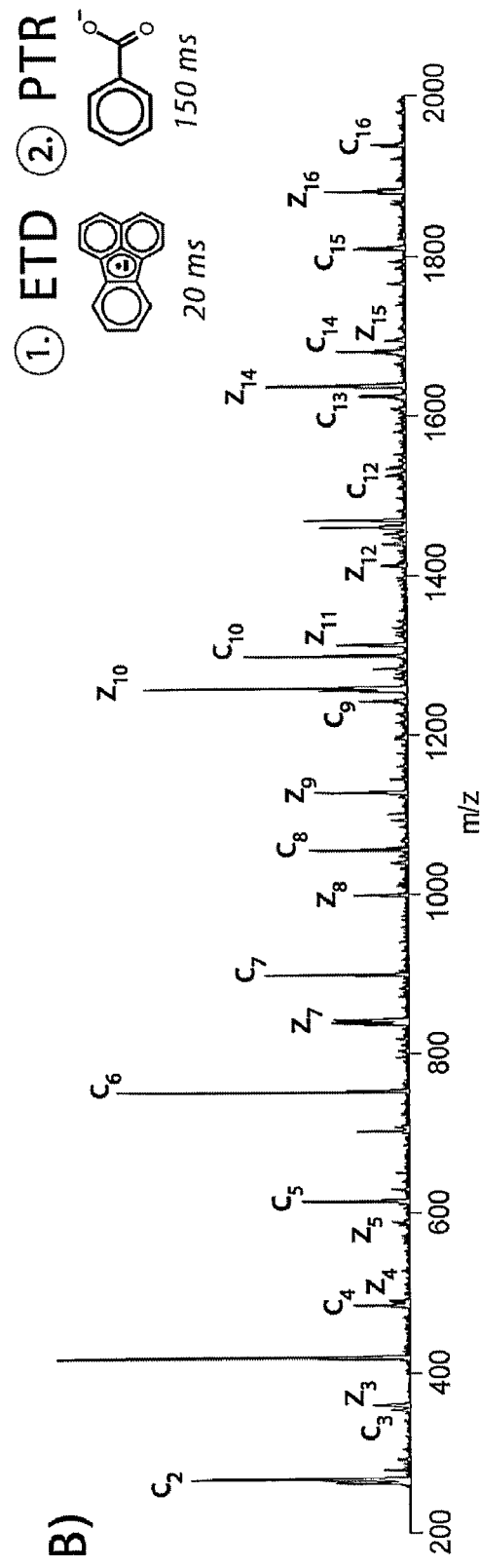
Fig. 8 A)
Fig. 8 B)

A) 100 scans (infusion, 60 sec)

B) 5 scans (chromatography, 3 sec)

SEQUENCE LISTING

<160> NUMBER OF SEQ ID NOS: 10

<210> SEQ ID NO 1
<211> LENGTH: 12
<212> TYPE: PRT
<213> ORGANISM: Artificial Sequence
<220> FEATURE:
<223> OTHER INFORMATION: Synthetic peptide for amino acid sequencing
<220> FEATURE:
<221> NAME/KEY: MOD_RES
<222> LOCATION: (8)..(8)
<223> OTHER INFORMATION: PHOSPHORYLATION
<220> FEATURE:
<221> NAME/KEY: MOD_RES
<222> LOCATION: (9)..(9)
<223> OTHER INFORMATION: PHOSPHORYLATION

<400> SEQUENCE: 1

Leu Pro Ile Ser Ala Ser His Ser Ser Lys Thr Arg
1               5                   10

<210> SEQ ID NO 2
<211> LENGTH: 52
<212> TYPE: PRT
<213> ORGANISM: homo sapiens

<400> SEQUENCE: 2

Ser Gly Arg Gly Lys Gly Gly Lys Gly Leu Gly Lys Gly Gly Ala Lys
1               5                   10                  15

Arg His Arg Lys Val Leu Arg Asp Asn Ile Gln Gly Ile Thr Lys Pro
            20                  25                  30

Ala Ile Arg Arg Leu Ala Arg Arg Gly Gly Val Lys Arg Ile Ser Gly
        35                  40                  45

Leu Ile Tyr Glu
    50

<210> SEQ ID NO 3
<211> LENGTH: 50
<212> TYPE: PRT
<213> ORGANISM: homo sapiens

<400> SEQUENCE: 3

Ala Arg Thr Lys Gln Thr Ala Arg Lys Ser Thr Gly Lys Ala Pro
1               5                   10                  15

Arg Lys Gln Leu Ala Thr Lys Ala Ala Arg Lys Ser Ala Pro Ala Thr
            20                  25                  30

Gly Gly Val Lys Lys Pro His Arg Tyr Arg Pro Gly Thr Val Ala Leu
        35                  40                  45

Arg Glu
    50

<210> SEQ ID NO 4
<211> LENGTH: 24
<212> TYPE: PRT
<213> ORGANISM: Homo sapiens

<400> SEQUENCE: 4

Ser Tyr Ser Met Glu His Phe Arg Trp Gly Lys Pro Val Gly Lys Lys
1               5                   10                  15

Arg Arg Pro Val Arg Val Tyr Pro
            20

<210> SEQ ID NO 5
<211> LENGTH: 76
<212> TYPE: PRT
<213> ORGANISM: homo sapiens

<400> SEQUENCE: 5

Met Gln Ile Phe Val Lys Thr Leu Thr Gly Lys Thr Ile Thr Leu Glu
1               5                   10                  15

Val Glu Ser Ser Asp Thr Ile Asp Asn Val Lys Ser Lys Ile Gln Asp
            20                  25                  30

Lys Glu Gly Ile Pro Pro Asp Gln Gln Arg Leu Ile Phe Ala Gly Lys
        35                  40                  45

Gln Leu Glu Asp Gly Arg Thr Leu Ser Asp Tyr Asn Ile Gln Lys Glu
    50                  55                  60

Ser Thr Leu His Leu Val Leu Arg Leu Arg Gly Gly
65                  70                  75

<210> SEQ ID NO 6
<211> LENGTH: 50
<212> TYPE: PRT
<213> ORGANISM: homo sapiens

<400> SEQUENCE: 6

Ala Arg Thr Lys Gln Thr Ala Arg Lys Ser Thr Gly Gly Lys Ala Pro
1               5                   10                  15

Arg Lys Gln Leu Ala Thr Lys Ala Ala Arg Lys Ser Ala Pro Ala Thr
            20                  25                  30

Gly Gly Val Lys Lys Pro His Arg Tyr Arg Pro Gly Thr Val Ala Leu
        35                  40                  45

Arg Glu
    50

<210> SEQ ID NO 7
<211> LENGTH: 16
<212> TYPE: PRT
<213> ORGANISM: Gallus gallus

<400> SEQUENCE: 7

Ala Gly Gly Lys Ala Gly Lys Asp Ser Gly Lys Ala Lys Ala Lys Ala
1               5                   10                  15

<210> SEQ ID NO 8
<211> LENGTH: 12
<212> TYPE: PRT
<213> ORGANISM: Gallus gallus

<400> SEQUENCE: 8

Ser Leu Ile Gly Lys Lys Gly Gln Gln Lys Thr Ala
1               5                   10

<210> SEQ ID NO 9
<211> LENGTH: 16
<212> TYPE: PRT
<213> ORGANISM: Gallus gallus

<400> SEQUENCE: 9

Ala Gly Gly Lys Ala Gly Lys Asp Ser Gly Lys Thr Lys Thr Lys Ala
1               5                   10                  15

<210> SEQ ID NO 10
<211> LENGTH: 12

-continued

```
<212> TYPE: PRT
<213> ORGANISM: Gallus gallus

<400> SEQUENCE: 10

Ser Leu Ile Gly Lys Lys Gly Gln Gln Lys Thr Val
1               5                   10
```

SIMULTANEOUS SEQUENCE ANALYSIS OF AMINO- AND CARBOXY-TERMINI

RELATED APPLICATIONS

This application is a U.S. national application under 37 C.F.R. §371(b) of International Application Serial No. PCT/US2005/036337 filed Oct. 7, 2005 which claims priority under 35 USC §119(e) to U.S. Provisional Application Ser. No. 60/617,125, filed Oct. 8, 2004, the disclosures of which are incorporated herein by reference.

GOVERNMENT RIGHTS

This invention was made with United States Government support under Grant Nos. GM37537, 1F32 RR018688-01, and AI 33993, awarded by the National Institutes of Health, as well as MCB-0209793 awarded by the National Science Foundation. The United States Government has certain rights in the invention.

BACKGROUND

The identification and characterization of proteins and peptides has become a significant part of modern biology, and mass spectrometry has become one of the most important techniques used for the analysis of peptides and proteins. Recently, a novel means of peptide ion dissociation, referred to as electron transfer dissociation (ETD) was described (Syka, J. E. P.; Coon, J. J.; Schroeder, M. J.; Shabanowitz, J.; Hunt, D. F. *Proceedings of the National Academy of Sciences of the United States of America* 2004, 101, 9528-9533; Coon, J. J.; Syka, J. E. P.; Schwartz, J. C.; Shabanowitz, J.; Hunt, D. F. *International Journal of Mass Spectrometry* 2004, in press 2004). In ETD anions are reacted with multiply protonated peptide/protein cations in a linear ion trap mass spectrometer. The result is the transfer of an electron from the anion to the peptide. Following electron transfer, the peptide dissociates through the same pathways accessed in electron capture dissociation (ECD) (Zubarev, R. A.; Kelleher, N. L.; McLafferty, F. W. *Journal of the American Chemical Society* 1998, 120, 3265-3266).

ETD is fast and efficient, allowing its direct implementation with chromatography for peptide sequence analysis. Furthermore, ETD dissociates intact proteins with similar efficiency as the smaller peptides described in earlier work (Syka, J. E. P.; Coon, J. J.; Schroeder, M. J.; Shabanowitz, J.; Hunt, D. F. *Proceedings of the National Academy of Sciences of the United States of America* 2004, 101, 9528-9533). FIG. 2 displays the products obtained following a 15 ms reaction of the ETD-inducing anion, fluoranthene, with the +10 cation of residues 1-52 of histone H4 (SGRGKGGKGLGKG-GAKRHRKVLRDNIQGITKPAIRRLARR GGVKRIS-GLIYE; SEQ ID NO: 2). Observed are hundreds of c and z-type fragment ions, many of which are multiply charged. In fact, most of these product ions are highly charged. To fully separate the multiple isotopic peaks associated with the fragment species requires m/z resolving power beyond that available from linear ion trap mass spectrometers. Direct ETD dissociation of large peptide/protein cations, including for example, residues 1-52 of histone H4, typically generate product ion spectra that are too complicated to yield sequence information. Namely, this limitation is due to the presence of dozens or hundreds of highly charged c and z-type fragments all clustered within the ~300-1000 m/z range. Thus, without introduction of a second mass analyzer (hybridization) capable of resolving this complicated mixture of fragment ions, the practical applicability of direct ETD fragmentation of large peptide/protein cation is somewhat limited, especially for sequencing a priori unknown proteins.

In addition to the recently discovered ETD reaction, another type of ion/ion reaction was described several years ago by McLuckey and co-workers (Stephenson, J. L.; McLuckey, S. A. *Analytical Chemistry* 1996, 68, 4026-4032; McLuckey, S. A.; Stephenson, J. L. *Mass Spectrometry Reviews* 1998, 17, 369-407). In that reaction, multiply charged peptide or protein cations are reacted with an anion that removes protons from the protein cation (proton transfer reactions, PTR). By removing protons from the highly charged protein cations the net charge of the protein is reduced. In this fashion, the charge state of the protein can be determined. McLuckey et al. have also used the PTR reaction to reduce the charge of protein fragment ions derived from collision-activated dissociation (CAD) (Reid, G. E.; McLuckey, S. A. *Journal of Mass Spectrometry* 2002, 37, 663-675; Reid, G. E.; Shang, H.; Hogan, J. M.; Lee, G. U.; McLuckey, S. A. *Journal of the American Chemical Society* 2002, 124, 7353-7362; Amunugama, R.; Hogan, J. M.; Newton, K. A.; McLuckey, S. A. *Analytical Chemistry* 2004, 76, 720-727).

Accordingly, highly charged b and y-type fragment ions derived from collision-activated dissociation can be reduced to singly charged species for easier interpretation. However, the use of CAD for the production of product ions suffers from several disadvantages including the following:

a) Peptides with post-translational modifications (i.e., phosphorylation and glycosylation, etc) often fragment by loss of the modification rather by cleavage of the peptide backbone. Only a relatively small percentage about (20%-30%) of these types of peptide ion precursors produce interpretable/searchable product ion spectra. This is somewhat lessened (less tendency for modification loss) as the number of amino acids in the peptide increases.

b) Peptides that contain multiple basic amino acid residues (Lys, Arg, and His) and thus carry more than two charges, also fail to fragment randomly along the peptide backbone and thus afford incomplete sequence information when analyzed by the above technology (CAD).

c) Peptides that contain more than 40 amino acids also fail to fragment randomly along the peptide backbone. These also afford incomplete sequence information.

Therefore, CAD fragmentation for protein cations usually does not provide adequate information regarding post-translational modification of the proteins and does not routinely cleave each peptide bond in the protein/large peptide. Typically only a few b and y-type cleavages are observed for large polypeptide species (e.g., greater than 40 amino acids) and the process is highly dependent upon the initial charge state of the protein (Hogan, J. M.; McLuckey, S. A. *Journal of Mass Spectrometry* 2003, 38, 245-256). Because of the random, non-predictable nature of CAD cleavage this type of experiment has not become a routine tool for whole protein sequence identification.

There is a long felt need in the art for the development of new methods for rapid sequence analysis of intact proteins or peptides or large protein degradation products. The present invention satisfies this need.

SUMMARY OF VARIOUS EMBODIMENTS

One aspect of the present disclosure is directed to a quick method of identifying, or confirming the presence of, a polypeptide present in a sample. In one embodiment the present invention allows the identification of a polypeptide, of at least 40 amino acids in length, through the use of a single linear ion trap mass spectrometer. The method comprises using mass spectrometer analysis to simultaneously identifying the amino acid sequence of the carboxy and amino termini of the polypeptide. ETD, as discussed above, often generates a complete or near complete set of cleavage products (c,z-type fragments) corresponding to cleavage of peptide backbone bonds for essentially all constituent amino acid residues (except Proline), regardless of peptide size or charge (assuming charge >3). As described herein, implementation of a subsequent ion/ion reaction (a proton transfer reaction; PTR) to charge reduce the highly charged c and z-type fragments produces an m/z spectrum containing a series of c and z-type fragment ions that are easily interpreted to reveal the sequence of the amino and carboxy terminus, respectively.

In accordance with one embodiment the method comprises introducing a protein, in a multiply charged cationic state, into an RF electric field ion containment device and mixing gas-phase electron transfer reagent anions with the protein, so as to facilitate electron transfer from the electron transfer reagent anions, to the protein, to produce dissociation product cations. The dissociation product cations are then contacted with proton accepting reagent anions, so as to facilitate proton transfer from said dissociation product cations to the proton accepting reagent anions, to reduce the charge on the multiply charged dissociation product cations so the final fragment cation population consists essentially of low charged, and in one embodiment, singly charged cations. Mass (m/z) analysis is then conducted on the singly charged fragments to determine the sequence of the amino and carboxy termini of the protein, and thus identify the protein. If necessary, the carboxy and amino termini sequences can be used to search a relevant protein sequence database to identify the protein. In one embodiment the identification of the protein is further delineated by making a mass spectrometric determination of the molecular weight of the intact protein.

BRIEF DESCRIPTION OF THE DRAWINGS

FIGS. 4A and 4B, depicts two types of ion/ion reactions: FIG. 5A represents a proton transfer reaction (PTR), and FIG. 5B represents an electron transfer dissociation reaction (ETD). FIG. 5A displays the products resulting from an ion/ion reaction of PDCH with the triply protonated phosphopeptide, LPISASHpSpSKTR (SEQ ID NO: 1). Here the PDCH anion removes protons from the peptide leaving the peptide charge reduced (+1 and +2 products). FIG. 5B displays the products resulting from the ion/ion reaction of fluoranthene anions with the same triply protonated peptide. Here extensive fragmentation of the peptide is observed. Rather than removing protons, as with the PDCH anion, fluoranthene anions donate electrons to the multiply protonated peptide. The electron addition induces peptide backbone cleavage and extensive dissociation.

FIG. 6B presents a later eluting version of the 50 amino acid residue. Here the precursor m/z is 580 with charge state +10. Again extensive c and z-type fragmentation were observed allowing characterization of both the amino and carboxy terminus of the polypeptide.

FIG. 7 shows a comparison of MS/MS spectra of the same +7 Adrenocorticotropic hormone (ACTH) peptide (SYSMEHFRWGKPVGKKRRP VRVYP$^{7+}$; SEQ ID NO: 4) (m/z 420) reacted with the anion of fluoranthene for a duration of ~75 ms (FIG. 7, top panel), and reacted with the anion of fluoranthene followed by reacting the resulting multiply charged product ions with anions of sulfur hexafluoride for about 200 ms (FIG. 7, lower panel).

FIGS. 8A & 8B shows a comparison of MS/MS spectra of the same +7 ACTH peptide (SYSMEHFRWGK-PVGKKRRPVRVYP$^{7+}$; SEQ ID NO: 4) (m/z 420) reacted with the anion of fluoranthene for a duration of about 20 ms (FIG. 8A), followed by reacting the resulting multiply charged product ions with anions of benzoic acid for about 150 ms (FIG. 8B).

FIGS. 10B-10D display the subsequent reaction of these products with even-electron anions of benzoic acid for 50, 100, and 150 ms, respectively. Note gradual degradation of multiply charged products leaving predominately doubly and singly charged fragments after 150 ms. FIG. 10E displays the resulting sequence coverage (MQIFVKTLTGKTITLEVESSDTIDNVK-SKIQDKEGIPPDQQRLIFAGKQLEDGR TLSDY- NIQKESTLHLVLRLRGG; SEQ ID NO: 5) considering only singly charged product ions. Each spectrum is the average of ~50 spectra (~30 second acquisition) and the y-axis indicates the relative ion abundance.

FIGS. 11B-11D display the resulting tandem mass spectra for ubiquitin, cytochrome c, and histone H2B, respectively. Each spectrum is the average of 4 single-scan mass spectra (~2 second acquisition) and the y-axis indicates the relative ion abundance.

FIG. 12A displays the tandem mass spectrum generated following direct analysis of the +49 charge state of albumin (~66 kDa) using sequential ion/ion reactions (~100 single-scan spectra, 60 second acquisition). Chromatographic elution of 100 fmol (on-column) of the same protein, with automated online sequential ion/ion reactions, generated the spectrum shown in FIG. 12B (5 single-scan spectra, ~3 second acquisition). The inset shown in FIG. 12B displays the protein charge envelope following ESI and denotes which m/z was selected for fragmentation (1187, +57). Note the extensive c-type ion series is readily interpreted to characterize the amino-terminus of the intact protein. The y-axis indicates the relative ion abundance, * denotes a doubly charged c or z-type fragment ion. No sequence ions, however, from the carboxy-terminus could be identified in the spectrum. Previous works have noted gas-phase protein conformation can affect the production, or at least, the observation of fragmentation following ECD. As protein size increases so does the possibility of partial or complete folding in the gas-phase (gas-phase conformation). Disulfide linkages, which cross link specific amino acids in the protein, can also prevent gas-phase protein unfolding. In this example, the disulfide linkages were allowed to remain intact prior to analysis. These linkages likely promoted the albumin ions to adopt a gas-phase conformation that prevented formation, or at least observation, of the low m/z z-type ions.

FIG. 13A displays the tandem mass spectrum generated from early eluting peptide. Note the extensive c and z-type ion series allows interpretation of the amino- and carboxy-termini and locates one site of methylation and two sites of dimethylation. Displayed in FIG. 13B is the tandem mass spectrum generated from a later eluting peptide. Here the c-type ion series indicates the N-termini is modified identically; however, the C-termini is monomethylated at $K_{37}$, as opposed to dimethylation of $K_{36}$ on the earlier eluting species. Note the spectrum shown in FIG. 13B contains fragment ions derived from a mixture of at least two uniquely modified peptides (the y-axis indicates the % relative ion abundance).

FIG. 14A shows a chromatograph of the intact histone H2A.Z protein. FIG. 14B displays the protein charge envelope of two co-eluting proteins and the corresponding m/z values that were selected for interrogation. FIG. 14C displays the resulting tandem mass spectrum following dissociation of the lighter m/z species—unmodified histone H2A.Z (AGGKAGKDSGKAKAKA (SEQ ID NO: 7) . . . SLIGKKGQQKTA (SEQ ID NO: 8). FIG. 14D displays the resulting tandem mass spectrum following dissociation of the heavier protein (AGGKAGKDSGKTKTKA (SEQ ID NO: 9) . . . SLIGKKGQQKTV (SEQ ID NO: 10). Comparison of the c and z-type fragment series indicates the presence of a new H2A.Z isoform with four amino acid substitutions. The y-axis indicates the relative ion abundance, *denotes a doubly charged c or z-type fragment ion.

DETAILED DESCRIPTION

Definitions

Figure 1:
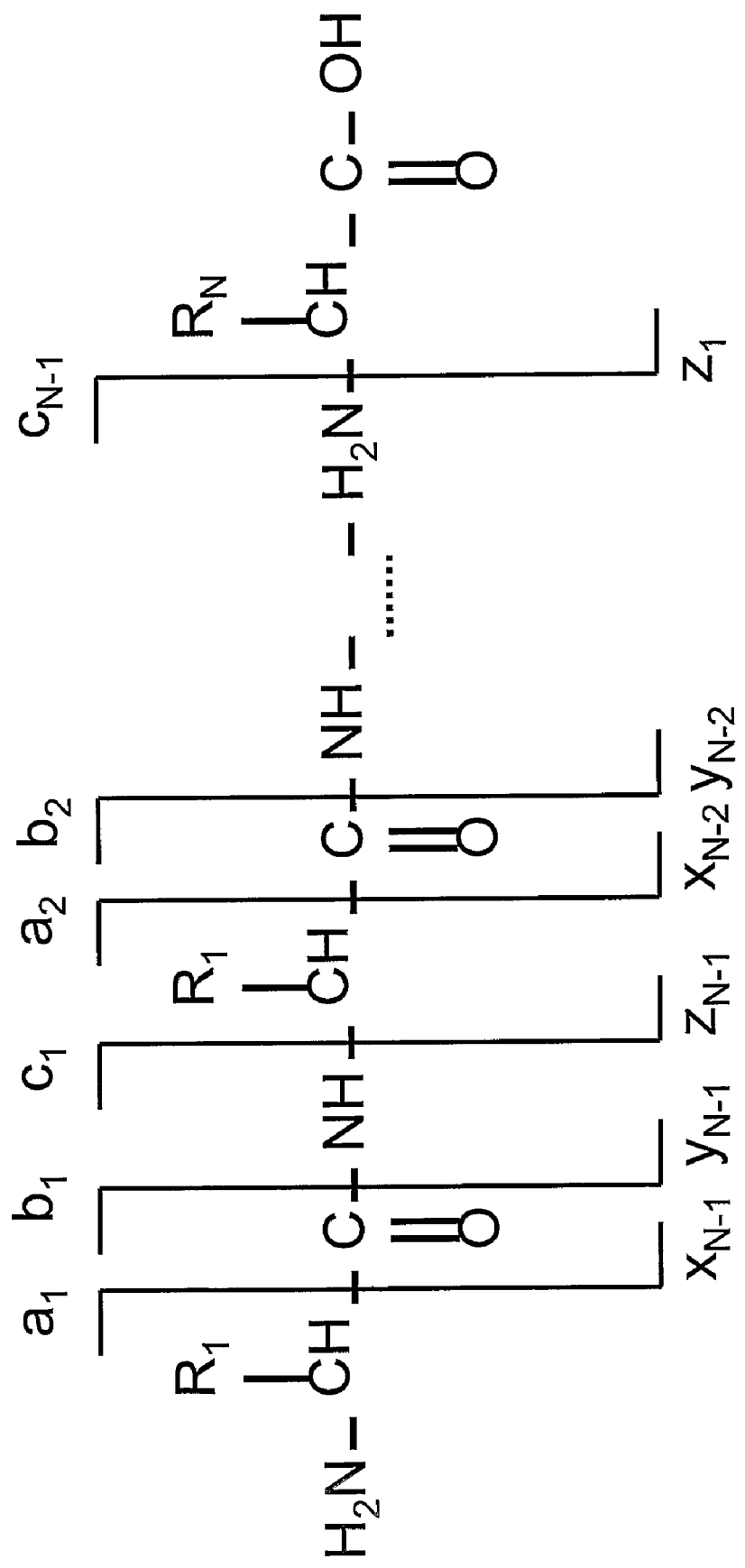
FIG. 1 is a schematic representation of the various types of peptide backbone cleavage produced by mass spectrometry peptide analysis and the associated nomenclature for the cleaved products. Note a, b, c-type fragment ions contain the amino-terminus, while x, y, z-type fragment ions contain the c-terminus of the precursor peptide ion. The low energy CAD process predominantly cleaves the amide linkage to form b/y-type pairs; ECD and ETD cleave the amine bond to form mostly c/z-type fragment ions.

As used herein, the term "halogen" or "halo" includes bromo, chloro, fluoro, and iodo.

The term "haloalkyl" as used herein refers to an alkyl radical bearing at least one halogen substituent, for example, chloromethyl, fluoroethyl or trifluoromethyl and the like.

The term "$C_1$-$C_n$ alkyl" wherein n is an integer, as used herein, represents a branched or linear alkyl group having from one to the specified number of carbon atoms. Typically $C_1$-$C_6$ alkyl groups include, but are not limited to, methyl, ethyl, n-propyl, iso-propyl, butyl, iso-butyl, sec-butyl, tert-butyl, pentyl, hexyl and the like.

As used herein the term "aryl" refers to a mono- or multi-cyclic carbocyclic ring system having one or more aromatic rings including, but not limited to, phenyl, benzyl, naphthyl, tetrahydronaphthyl, indanyl, indenyl, anthracenyl and the like. "Optionally substituted aryl" includes aryl compounds having from zero to four substituents, and "substituted aryl" includes aryl compounds having one to three substituents, wherein the substituents include hydroxyl, $C_1$-$C_4$ alkyl, halo or amino substituents.

The term "polyaromatic hydrocarbon" refers to a multi-cyclic carbocyclic ring system comprising two or more aromatic rings (selected from aryl and heteroaryl ring structures), and including but not limited to napthalene, fluorene, phenanthrene, pyrene, fluoranthene, chrysene, triphenylene, perylene, acridine; 2,2' dipyridyl; 2,2' biquinoline; 9-anthracenecarbonitrile; dibenzothiophene; 1,10'-phenanthroline; 9' anthracenecarbonitrile; and anthraquinone. "Substituted polyaromatic hydrocarbon" includes polyaromatic hydrocarbon compounds having one to three substituents, wherein the substituents include aryl, heteraryl, hydroxy, $C_1$-$C_4$ alkyl, halo, —CN, or amino substituents.

The term "heterocyclic group" refers to a mono- or multi-cyclic carbocyclic ring system containing one or more heteroatoms wherein the heteroatoms are selected from the group consisting of oxygen, sulfur, and nitrogen.

As used herein the term "heteroaryl" refers to a mono- or multi-cyclic carbocyclic ring system having one or more aromatic rings containing one or more heteroatoms (such as O, N and S) and includes, but is not limited to, furyl, thienyl, pyridyl and the like.

As used herein the term "macromolecule" refers to polymers of monomeric units or derivatives thereof, including synthetically derived polymers as well as naturally occurring polymers. Examples of macromolecules include polypeptides, polysaccharides, and nucleic acids.

The terms "polypeptide" and "protein" refer to a polymer of amino acids of at least 30 amino acids in length. This term does not specify or exclude chemical or post-expression modifications of the polypeptides of the invention, although chemical or post-expression modifications of these polypeptides may be included or excluded as specific embodiments.

Modifications to polypeptides include the covalent attachment of glycosyl groups, acetyl groups, phosphate groups, lipid groups, ubiquitin groups and the like are expressly encompassed by the term polypeptide. Further, polypeptides with these modifications may be specified as individual species to be included or excluded from the present invention. The modifications of the polypeptides can occur anywhere in a polypeptide, including the peptide backbone, the amino acid side-chains and the amino or carboxyl termini. It will be appreciated that the same type of modification may be present in the same or varying degrees at several sites in a given polypeptide. (See, for instance, PROTEINS—STRUCTURE AND MOLECULAR PROPERTIES, 2nd Ed., T. E. Creighton, W. H. Freeman and Company, New York (1993); POST-TRANSLATIONAL COVALENT MODIFICATION OF PROTEINS, B. C. Johnson, Ed., Academic Press, New York, pgs. 1-12 (1983); Seifter et al., Meth Enzymol 182:626-646 (1990); Rattan et al., Ann NY Acad Sci 663:48-62 (1992)).

As used herein the phrase "determination of an amino acid sequence" is intended to include direct determination of the contiguous amino acid sequence, as well as a determination of a partial and/or non-contiguous sequence of a target protein, as well as the use of partial and/or non-contiguous sequences of a target protein to identify the complete sequence based on a nucleic acid or protein database search as well as identification of a protein by direct comparison of observed fragment ion masses with those expected fragments derived from known amino- and carboxy-terminal sequences of known proteins.

As used herein the phrase "determination of an amino-terminal sequence" and "determination of a carboxy terminal sequence" are intended to include the determination of an amino acid sequence of any length greater than 2, that is within 10 amino acids of the respective amino or carboxy terminus of the protein.

As used herein the term "introducing" a cation or anion, when used in the context of an ion containment device, encompasses physically inserting the ions into the containment device, as well as initiating the contact of the cations with the reagent anions. For example, introducing the ions may include the step of contacting cations and reagent anions already present in the containment device, but sequestered, by moving sequestered ions into contact within on another. Similarly, the term "removing cations/anions" will be defined as ending the contact of the cations with the reagent anions. For example, the removal of ions includes the physical removal of one of the ions from the containment device as well as the sequestering of cations and reagent anions from one another with both ions remaining within the containment device.

Embodiments

In accordance with the present disclosure a method is provided for conducting rapid amino and carboxy-terminal sequence analysis of intact proteins or large protein degradation products using mass spectrometry and multiple ion/ion reactions. In one embodiment the method provides a rapid means for identifying or confirming the presence of a polypeptide of 30, 40, 50 or more amino acids in length in a sample. The sample may contain the target polypeptide in pure form (e.g., greater than 99% pure) or may include other polypeptides or compounds. The sample could also be derived from a complex mixture of other proteins/peptides, e.g., whole cell lysate. More particularly, in one embodiment the method comprises the steps of conducting a first ion-ion reaction (electron transfer dissociation reaction: ETD), to effect the dissociation of polypeptide ions in a mass spectrometer system, followed by a second ion-ion reaction (proton transfer reaction: PTR) that results in a charge reduction of the ion fragments. This reduction in charge simplifies the mass spectral analysis of the ions and allows for a relatively quick deduction of the polypeptide's amino and carboxy terminal amino acid sequences.

As described herein the determination of the amino and/or carboxy terminus does not require that the complete contiguous sequence of amino acids be established for the carboxy and amino termini. Rather this phrase simply intends to convey that a sufficient number of amino acid residues, and their positions, (or observed fragment ion masses) have been determined within the neighborhood of the carboxy and amino termini, that only a relatively few proteins (or relatively few proteins having a predicted fragment ion masses) can be correlated with the identified amino acid sequence (or observed fragment ion masses). The sequences derived from the mass spectrometer analysis may have one or more gaps or indeterminate amino acids. Ideally, the sequence information will allow a database search to identify only one or two proteins that match the identified sequence. Accordingly, identification of the protein is independent of explicit determination of the carboxy and amino termini of the protein. As long as a sufficient number of the true c and z-type ions (which include the amino- or carboxy-termini of the precursor) that have lengths between 1 to about 10 or even about 20 amino-acid residues then there is sufficient information to identify the protein or at least produce a list of closely related proteins that have either identical amino- or carboxy-terminal sequences via data base searching methods. Furthermore, the derived sequence information can be combined with the approximate molecular weight of the protein, as determined by mass spectrometer analysis, to further assist in identifying the protein.

One aspect of the present method is that the dominant ions in the product ion spectrum can be expected to carry information that is specific to the carboxy- and amino-termini of the protein. There often will be other low charge and "low" mass ions mixed in with carboxy- and amino-terminal ions that are probably internal fragment ions—the products of multiple ETD reactions which contain neither the carboxy- and amino-termini of the protein. For very highly charged precursor ions the ETD reaction rate is so high (the rate of such ion-ion reactions go as the square charge state of the ions) that unless the number of reagent anions is restricted, the product ions generated in even the short reaction times (1-5 ms) are the products of multiple ETD reactions. Each original large polypeptide ion precursor is therefore partitioned into multiple peptide fragment ions, two of which must include either terminus of the original protein precursor. The ETD products from an initial population of precursor ions (the total charge of the precursor ion population would typically be on the order of 10,000-100,000 charges—for a +25 precursor that would be 400 to 4000 precursor ions) every precursor ion will produce a set of true c-type (N-terminal) fragment and a set true z-type (C-terminal) fragment as well as a large number of internal fragments that will have a variety of masses. The amino- and carboxy-terminal fragment ions simply get shorter and relatively more abundant as the number of ETD reactions is increased. It should be noted that the long intermediate amino- amino- and carboxy-terminal fragments will be more highly charged than the short ones and will therefore react faster than the short amino- and carboxy-terminal products. Unless something is done to inhibit the ETD reactions (depletion of the reagent anions There will be a minor abundance of ions associated with every possible internal fragment of each length).

In aggregate the internal fragments will have a quasi-random distribution of masses since ETD, with the exception of cleavage at Proline, produces cleavage that is substantially independent of residue type. Attempts to use the "high" m/z range mode of one instrument, which allows analysis of ions at reduced resolution and reduced sensitivity to a m/z range of 4000, led to difficulty distinguishing the true c and z-ions from the internal fragment "noise" ions in the product ion mass spectrum (after charge reduction) at m/z above 2000 (the standard m/z range for unit resolution scan mode and higher resolution scan modes). At lower masses the c and z-type product ions standout sufficiently above the internal "noise" peaks to be readily discernable.

Surprisingly, good amino- and carboxy-terminal sequence ions can be obtained from large species when the ETD reaction goes sufficiently long enough to produce products that are concentrated within our limited mass range. In accordance with one embodiment the present method allows for the determination of carboxy and amino termini for precursor ions having masses greater than 5,000 Daltons, and in one embodiment, precursor ions having masses greater than 10,000. Accordingly, the present method enables determination of carboxy and amino termini sequence using mass spectrometers of unit resolution and ordinary mass range (most RF ion trap instruments in their standard scan mode provide unit resolution and a m/z range of about 2000 dalton/unit charge). In addition as described above, not every consecutive sequence ion of the carboxy or amino termini needs to be identified in the mass spectra to identify the protein (see Example 4). For example, if 5 or 6 consecutive sequence ions can be obtained within the first 12 to 18 residues from each end of the polypeptide that is plenty of information for the ID by semi automated methods (manually get the 6 residue sequence and then search the sequence tag in a database). In practice for polypeptides that fragment well, most of the sequence ions are in the spectra and they can provide polypeptide identification via direct data base matching (using a modified version of the OMMSA program) that have very low expected false positive rates. In accordance with one embodiment at least 50% (or in another embodiment, at least 70%) of the masses (not m/z) of the fragment ion m/z peaks utilized for sequence determination/protein identification are less than 2000 Daltons. In accordance with one embodiment at least 70% of the masses (not m/z) of the fragment ion m/z peaks utilized for sequence determination/protein identification are less than 1500 Daltons. In accordance with one embodiment at least 70% of the masses (not m/z) of the fragment ion m/z peaks utilized for sequence determination/protein identification are less than 1000 Daltons.

In accordance with one embodiment a method is provided for determining amino and carboxy terminal amino acid sequences of a large polypeptide. In one embodiment the polypeptide to be analyzed is at least 30 amino acids in length. In another embodiment the polypeptide is at least 40 amino acids in length. In another embodiment the polypeptide is at least 50 amino acids in length. The polypeptide is ionized to form a multiply charged cation, typically by electrospray ionization and the cation is dissociated by ETD. The resulting fragments are then charge reduced to a low unit charge of 4 or lower. In one embodiment the charged c and z-type fragments produced by the ETD reaction are contacted with a proton accepting reagent ions for a time sufficient to reduce the charge of the dissociation fragments so the remaining fragments consist essentially of fragments having three or fewer unit charges. In one embodiment the charged c and z-type fragments produced by the ETD reaction are contacted with a proton accepting reagent ions for a time sufficient to reduce the charge of the dissociation fragments so the remaining fragments consist essentially of fragments having two or fewer unit charges. Once the charge reduction step has been completed the remaining charge fragments are subjected to mass (m/z) analysis.

More particularly, in accordance with one embodiment, the method for determining amino and carboxy terminal amino acid sequences of a large polypeptide comprises the steps of introducing the polypeptide into an RF electric field ion containment device, wherein the polypeptide is in a multiply charged cationic state, introducing gas-phase electron transfer reagent anions into said ion containment device, mixing the introduced electron transfer reagent anions, or derivative electron transfer reagent ions thereof, and the polypeptide, so as to facilitate electron transfer from the electron transfer reagent anions, or derivative electron transfer reagent ions thereof, to the polypeptide, to produce dissociation product cations. A gas-phase proton accepting reagent anions is then introduced into the ion containment device and the introduced proton accepting reagent anions, or derivative proton accepting reagent ions thereof, and the dissociation product cations are mixed, so as to facilitate proton transfer from said dissociation product cations to the proton accepting reagent anions, or derivative proton accepting reagent ions thereof, to reduce the charge on the multiply charged dissociation product cations so the remaining charged c and z-type fragments consist essentially of fragments having four or fewer unit charges. The remaining charged fragments are then subjected to mass (m/z) analysis, and the amino and carboxy sequences of the polypeptide are determined using this data. In accordance with one embodiment, the method further comprises the step of removing the electron transfer reagent anions, and electron transfer derivative reagent ions thereof, prior to the introduction gas-phase proton accepting reagent anions. In one embodiment the initial intact polypeptide has a mass of at least 5000 Daltons, and in a further embodiment, the polypeptide has a mass of at least 10,000 Daltons. In another embodiment the PTR reaction is conducted for a length of time so that the charged c and z-type fragments remaining after termination of the PTR consist essentially of fragments having three or fewer unit charges. In another embodiment the PTR reaction is conducted for a length of time so that the charged c and z-type fragments remaining after termination of the PTR consist essentially of fragments having two or fewer unit charges, and in one embodiment the remaining charged c and z-type fragment ions consist essentially of singly charged fragments.

In accordance with one embodiment the step of mass (m/z) analyzing the low charged fragments is performed with an RF ion trap mass (m/z) analyzer. In one embodiment the RF ion trap mass (m/z) analyzer is one selected from the group consisting of a 3D RF ion trap analyzer and a linear ion trap analyzer. In another embodiment the step of mass (m/z) analyzing the low charged fragments is performed with a Fourier Transform ion cyclotron resonance (FTICR) mass (m/z) analyzer. In another embodiment the step of mass (m/z) analyzing the low charged fragments is performed with a time-of-flight mass (m/z) analyzer. In another embodiment the step of mass (m/z) analyzing the low charged fragments is performed with an orbitrap mass (m/z) analyzer.

Identification of the original protein can be further assisted by determining the mass of the intact precursor ion. The molecular weight of the precursor can be established by standard techniques known to those skilled in the art, such as from the distribution of m/z peaks in the full mass spectrum that are associated with the different charge states of the precursor molecule. Alternatively, a particular precursor m/z can be isolated and subjected to a PTR such the product ions of several different charge states are produced (but still within the m/z range of the instrument). The molecular mass (Daltons) of the precursor can be readily estimated from such data with accuracies generally well better than of +/−1.0% (probably closer to 0.1%) using or linear trap instrument in the unit resolution mode. Adding molecular weight information improves the certainty of the result by reducing the false positive rate.

In accordance with one embodiment determination of the amino- and carboxy-termini in conjunction with the molecular weight of the protein can be used to detect the presence of either post-translational modifications or splice variants of known proteins. More particularly, the original electrospray ionization spectrum affords signals from which one can calculate the molecular weight of the protein. Database searches with amino-terminal and carboxy-terminal sequence information will identify the protein being analyzed. If the molecular weight fails to match the protein identified by the sequence database search, then one concludes that the protein is post-translationally modified or exists as one of several splice variants. Detection of splice variants is an important aspect of the ETD capability as the older approach of digesting the protein and analyzing the peptides may or may not detect fragments that are unique to a specific splice variant.

In another embodiment the present method can be used to characterize compositions comprising recombinant proteins and antibodies produce as commercial products of the biotechnology and pharmaceutical industry. The US Food and Drug Administration's approval usually requires that the companies provide evidence that the products have not been truncated at the amino- or carboxy-termini during production. The method described herein now becomes the method of choice for generating this information. The companies must also show that the product is not contaminated with proteins from the cloning organism (bacteria, yeast, etc). The methods disclosed herein for analyzing a protein sample should also identify all protein contaminants in the commercial sample.

In one embodiment, the intact protein to be identified is ionized via electrospray ionization, a process that results in the formation of a highly-charged intact protein ion. Multiply charged protein ions are then accumulated in a linear ion trap mass spectrometer and subjected to an ion/ion reaction with a selected anion that is capable of inducing electron transfer dissociation. That reaction proceeds rapidly (ca. 1-50 ms) and causes extensive fragmentation of the peptide backbone, resulting in the formation of highly charged c and z-type fragment ions. Upon completion of the first ion/ion reaction, the ETD-inducing anions are removed and replaced with a second set of anions that are capable of charge reduction (10-250 ms). The purpose of those anions is to remove the excess charge from the multiply charged fragments created by ETD.

In one embodiment of the invention, the duration of the second ion/ion reaction is adjusted so that upon completion, essentially only singly charged c and z-type fragments remain. Finally, the second anion is removed and an m/z analysis of the resulting c and z-type ions is performed. The generated mass spectrum then contains a c and z-series of fragment ions. Subtraction of neighboring ions in the c series allows one to deduce the sequence of the protein amino terminus; likewise, subtraction of ions in the z series allows sequence analysis of the carboxy terminus.

In one embodiment, the initial large peptide/protein precursor ion population is much larger than the initial anion population, reducing the probability that product ions will undergo secondary charge transfer reactions and produce "internal" fragment ions. At the end of the reaction, the unreacted precursor ions are eliminated from the trap so their associated space charge does not interfere with the function of the mass analyzer.

Figure 3:
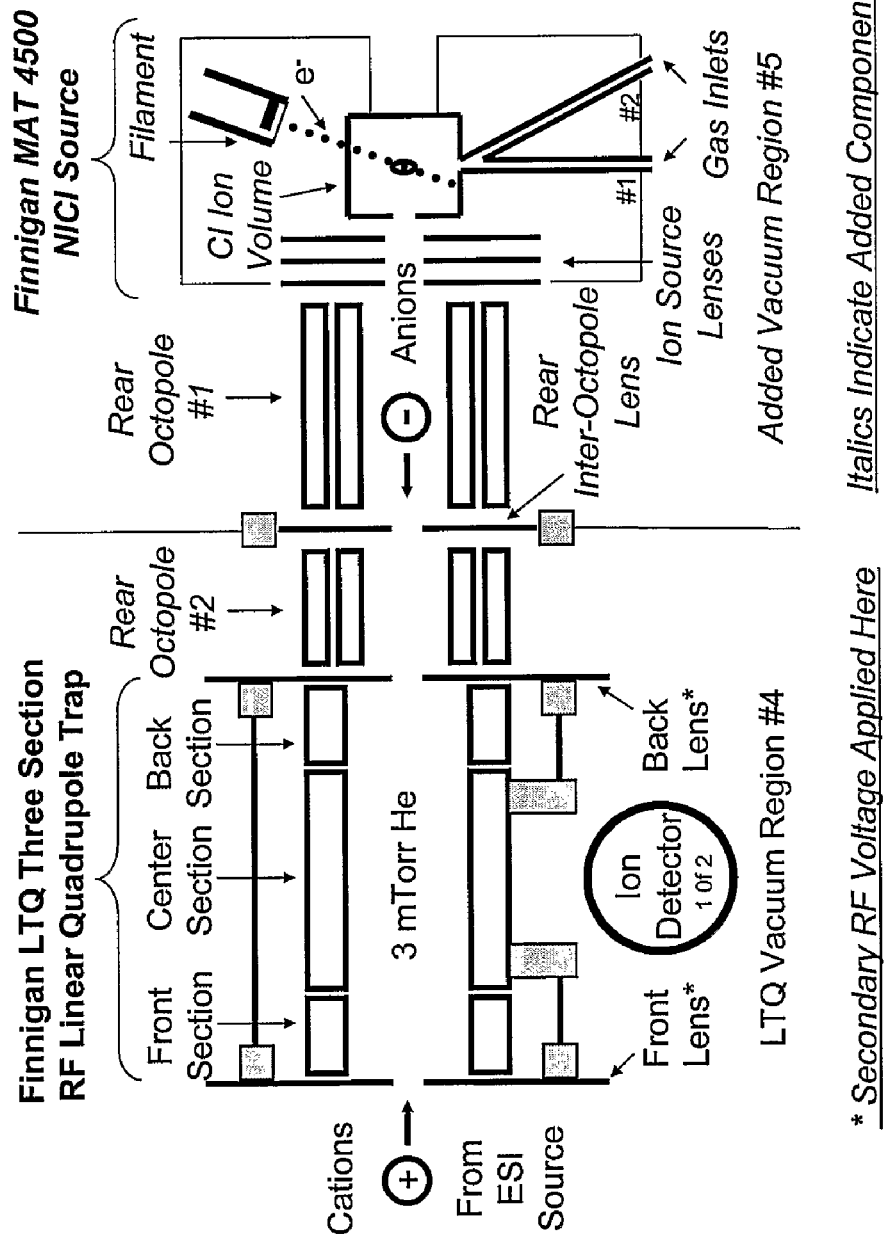
FIG. 3 represents a schematic drawing showing the instrumental setup and components added to the Finnigan LTQ. The NICI ion source (shown on the right) is interfaced with the linear ion trap by the addition of two octopoles and an inter-octopole lens. These added features serve to produce and transport anions into the linear ion trap.
Figure 4:
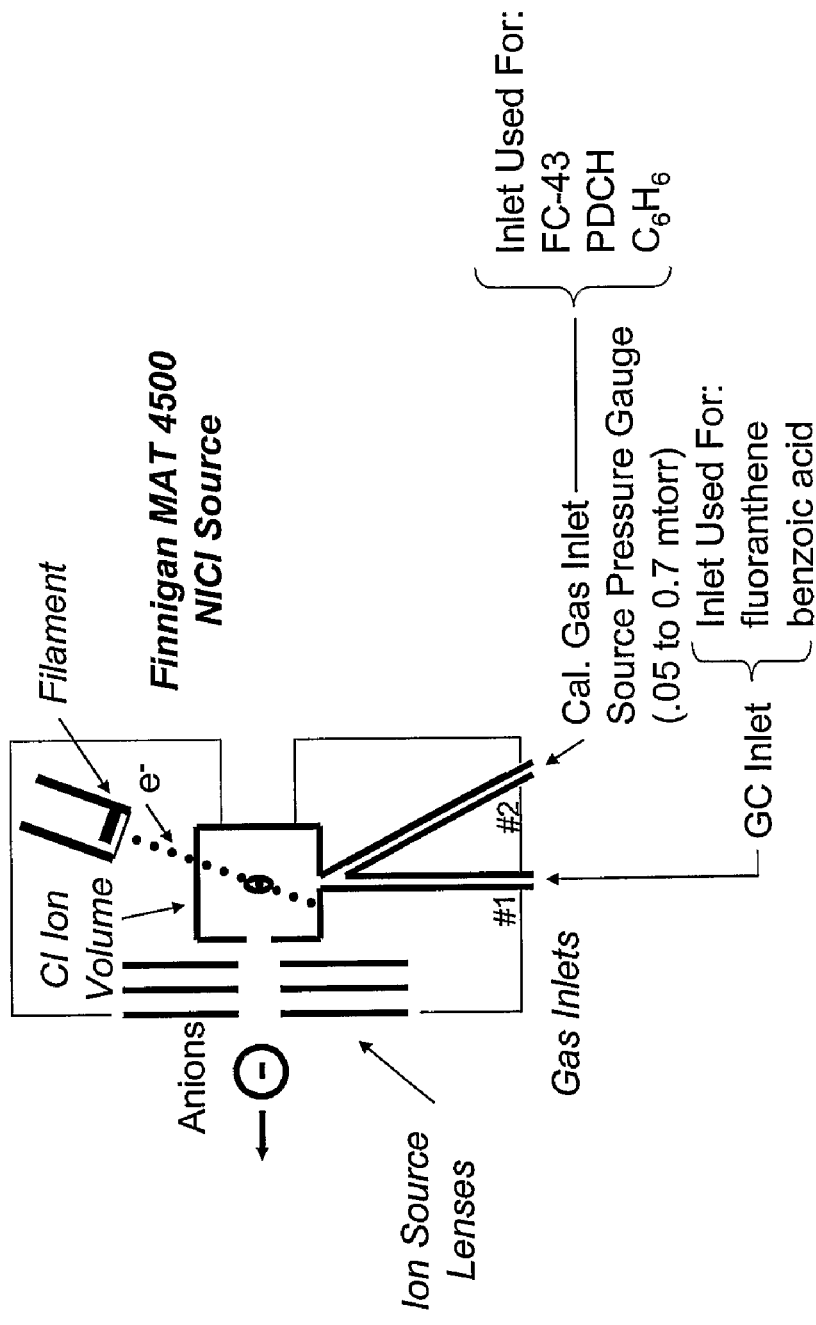
FIG. 4 represents a schematic inset of the Finnigan MAT 4500 NICI source used to generate anions.

Accordingly, one aspect of the present invention is directed to a sequential ion/ion reaction for amino- and carboxy-terminal protein sequencing which allows for rapid protein identification. The method utilizes ion/ion reaction of the protein cation of interest with two types of anions: anions that induce ETD and those that induce PTR. Both types of anions can be generated simultaneously in a chemical ionization (CI) source using methane as the reagent gas (see FIGS. 3 and 4). Electron bombardment of methane at 0.7 torr pressure with 70 eV electrons generates $CH_4^+$, $CH_3^+$ and a population of near thermal electrons. In one embodiment, to produce anions for both reactions, molecules of fluoranthene and benzoic acid are vaporized into the chemical ionization source and allowed to react with a population of thermal electrons (Hunt, D. F.; Stafford, G. C.; Crow, F. A.; Russell, J. W. Analytical Chemistry 1976, 48, 2098; Hunt, D. F.; Crow, F. A. Analytical Chemistry 1978, 50, 1781-1784). Examples of the reactions are shown below. A variety of anions have been tested and they can be broadly divided into two categories: those that react with multiply protonated peptides to transfer an electron (ETD), leading to the dissociation of the reduced charge cation species, and those that remove protons from multiply protonated peptides/proteins (proton transfer, PTR), without dissociation.

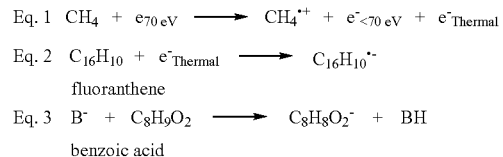

In one embodiment the sequential ion/ion reactions are conducted by first protonating large peptides and whole proteins, using electrospray ionization, for example. The multiply charged polypeptides are then injected along the linear axis from one end of a segmented 2D-multipole ion trap and stored in the front segment. Negative ions are then injected along the linear axis of the same segmented-2D-multipole trap, but from the opposite end. The anions derived from benzoic acid, and all others except those from fluoranthene and any background anions too near in m/z to the precursor polypeptide m/z to be removed without loss of the precursor polypeptides, are removed from the center section of the ion trap. The anions of fluoranthene are stored in the center segment of the linear ion trap and then allowed to mix with the multiply protonated protein ions. After a defined reaction period, the fluoranthene anions are axially ejected, while the cation products are moved back to the front section of the ion trap.

Unreacted precursor cations and undissociated products may also be selectively eliminated from the trap (typically via resonant ejection). Then anions are once again injected into the center section of the linear ion trap. This time the anions of fluoranthene are selectively removed from the center section of the linear trap leaving those from benzoic acid and a lower number of background anions. The anions of benzoic acid, initially stored in the center section, are allowed to mix with the c and z-type fragments produced from the prior ETD reaction. After another defined reaction period, the benzoic acid anions are axially ejected and finally an m/z analysis of the c and z-type products is conducted.

Two types of reactions may occur when a multiply charged (protonated) peptide, $(M+nH)^{+n}$, either encounters an odd-electron radical anion, $A^{\bullet-}$ (like those of fluoranthene), or an even electron anion, $A^-$ (like those of benzoic acid). Consider a multiply protonated protein cation where the number, n, is an integer that defines the initial number of charges on the precursor ion (>2). Primarily two reactions which involve either electron transfer (Eqs 7 and 10) or proton transfer (Eqs 8 and 9), have been observed, as outlined below. It has been proposed that electron transfer reactions (Eqs 7 and 10) produce hydrogen radicals which initiate the peptide backbone fragmentation observed under ETD conditions. Proton transfer reactions (Eqs 8 and 9) reduce the charge on the peptide, but fail to promote fragmentation.

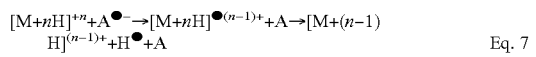  Eq. 7

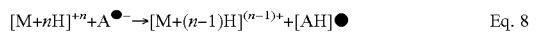  Eq. 8

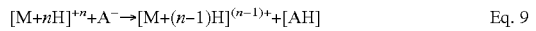  Eq. 9

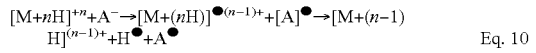  Eq. 10

Associative reactions have also been observed where the cations and anions form bound complexes which may subsequently dissociate to produce various product ions.

Figure 5A:
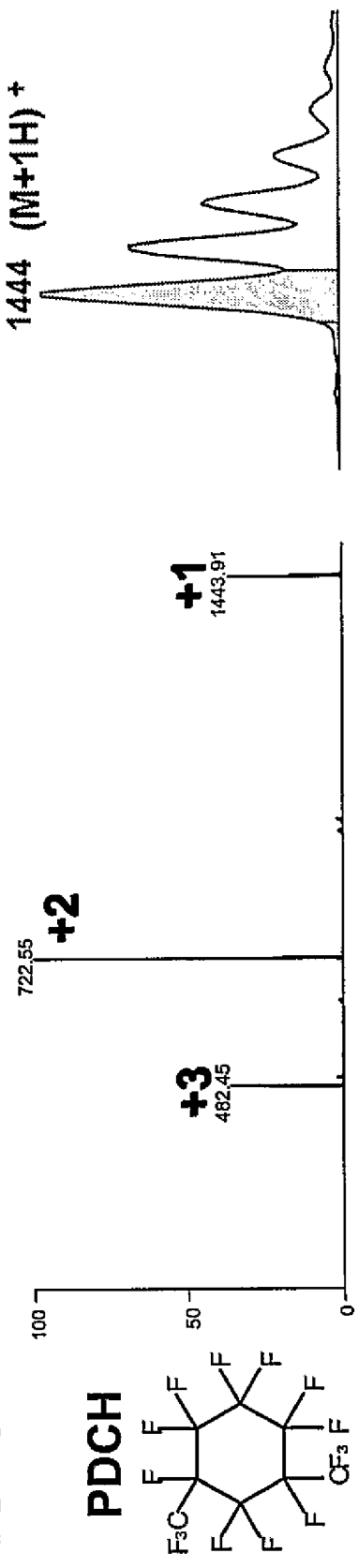
FIGS. 5A and 5B comprising
Figure 5B:
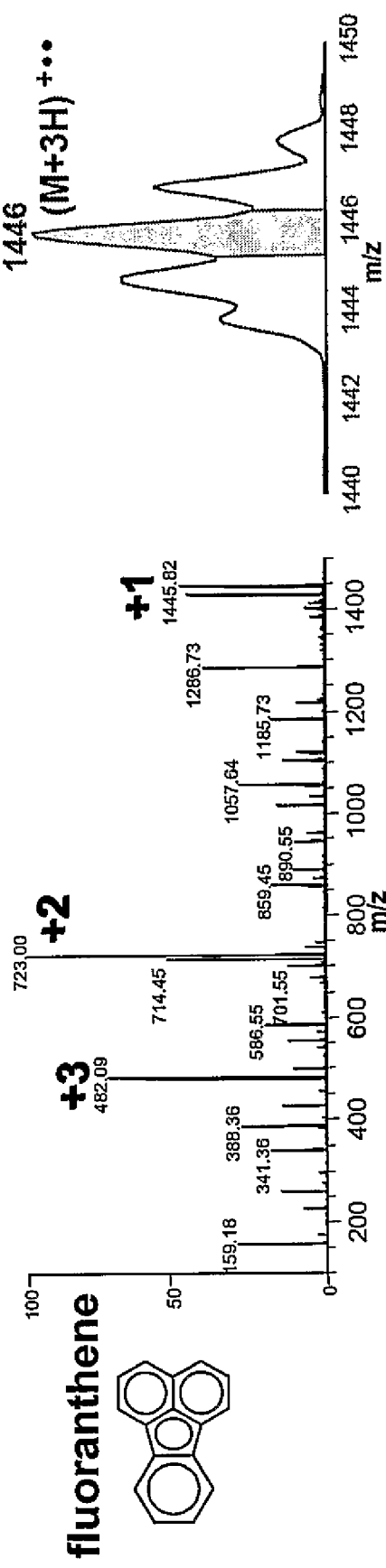

Fluoranthene performs particularly well in promoting the reaction defined in Equation 7. Conversely, anions of benzoic acid react exclusively via the pathway outlined in Equation 9. FIGS. 5A & 5B display ion/ion reactions of both anions (separately) with a triply protonated phosphopeptide. FIG. 5A displays the products resulting from an ion/ion reaction of PDCH (~100 ms), where the PDCH anion removes protons from the peptide leaving the peptide charge reduced (+1 and +2 products). FIG. 5B displays the products resulting from the ion/ion reaction of fluoranthene anions (~65 ms) with the same triply protonated peptide. Following this reaction extensive fragmentation of the peptide is observed. Rather than removing protons, as with the PDCH anion, fluoranthene anions donate electrons to the multiply protonated peptide. The electron addition induces peptide backbone cleavage and extensive dissociation.

Figures 6A, 6B:
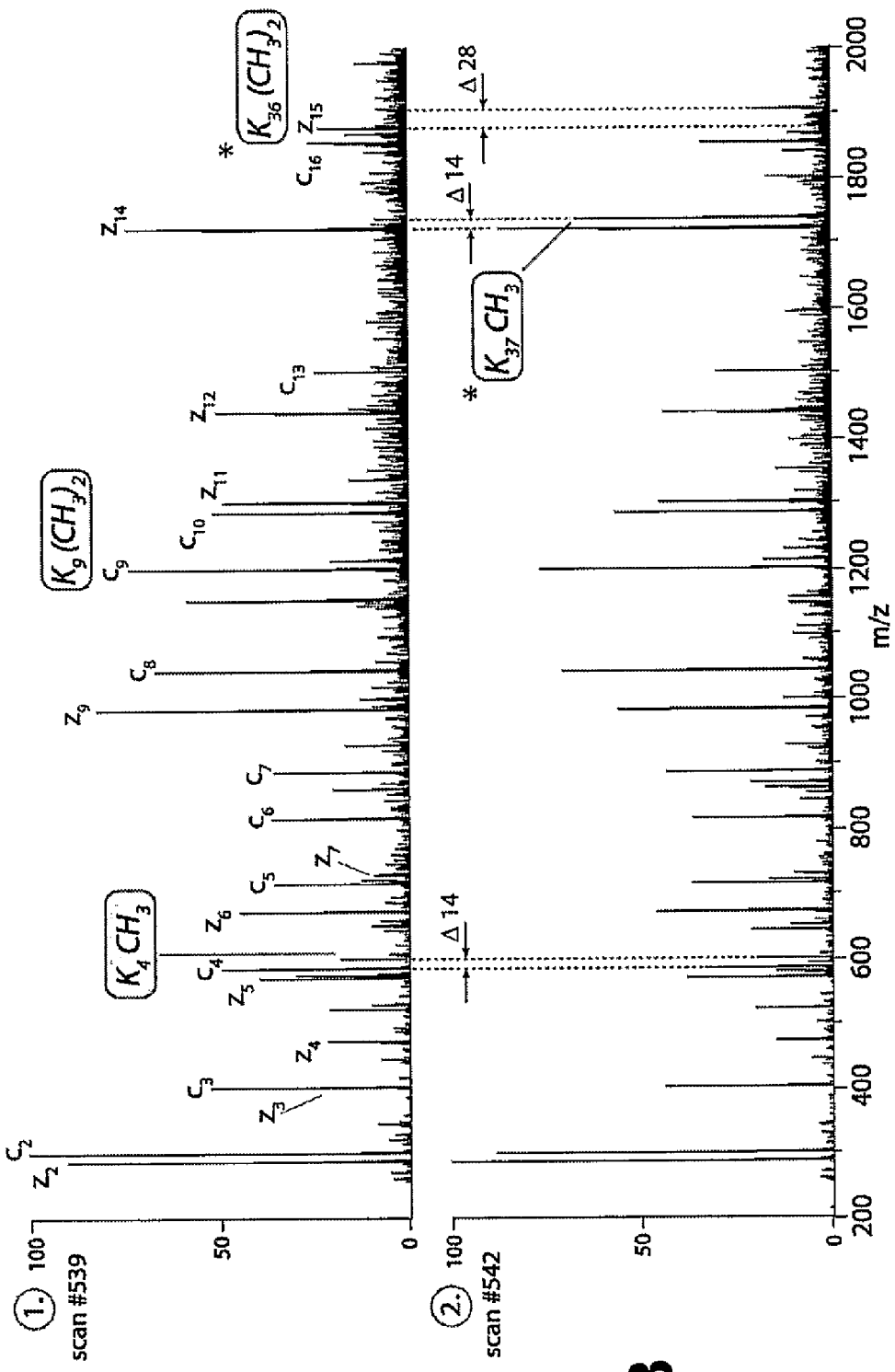
FIGS. 6A and 6B, depict product ion mass spectra resulting from sequential ion/ion reactions of fluoranthene and benzoic acid, respectively, with the +10 charge state of a 50 residue polypeptide from human histone H3 (ARTKQTARKSTG-GKAPRKQLATKAARKSAPATG-GVKKPHRYRPGTVALRE; SEQ ID NO: 3) (these spectra are the average of 5 scans, ~2 sec acquisition time). A complex mixture of different post translationally modified versions of the polypeptide (the protein is generally extensively post-translationally modified and occurs in cells as many hundreds of differentially modified variants) was loaded onto a microcapillary reversed-phase separation column and eluted with a gradient over a 60 minute period. The product ion spectrum from an early eluting peptide, having m/z 577 and charge state +10, is presented in FIG. 6A. These products result from an initial ion/ion reaction of m/z 577 with the radical anion of fluoranthene for 15 ms, followed by a second ion/ion reaction with anions from benzoic acid for 150 ms.

FIGS. 6A & 6B display product ion mass spectra resulting from sequential ion/ion reactions of fluoranthene/benzoic acid, respectively, with the +10 charge state of a 50 residue polypeptide from human histone H3 (1-50) (these spectra are the average of 5 scans, ~2 sec acquisition time). A complex mixture of the polypeptide (the protein is typically extensively post-translationally modified and typically is present in a cell in a very large number of different post-translational modified variants) was loaded onto a microcapillary reversed-phase separation column and eluted with a gradient over a 60 minute period. The product ion spectrum from an early eluting polypeptide variant, having m/z 577 and charge state +10, is presented in FIG. 6A. These products result from an initial ion/ion reaction of m/z 577 with the radical anion of fluoranthene for 15 ms, followed by a second ion/ion reaction with anions from benzoic acid for 150 ms. From the spectrum, a near-complete series of c-type ions extending to the 16th residue from the amino terminus was observed. Additionally, every possible z-type ion is observed through the 15th residue of the carboxy terminus. All these product ions are detected as singly protonated species. Furthermore, the spectrum contains few, if any, multiply charged c and z-type product ions. Since the presence of any substantial amount of multiply protonated fragments can be discounted, interpretation of the product ion mass spectrum is straightforward.

FIG. 6B presents a later eluting version of the 50 amino acid polypeptide. Here the precursor m/z is 580 with charge state +10. Again extensive c and z-type fragmentation is observed allowing characterization of both the amino and carboxy terminus of the polypeptide. Comparison of the two spectra reveals the following PTMs: Peptide #1 methylation of lysine 4, dimethylation of lysine 9 and 36; Peptide #2 methylation of lysine 4, dimethylation of lysine 9 and methylation of lysine 37. Here we provide evidence that, beyond identifying the sequence of the amino and carboxy terminus of polypeptide/protein cations, the sequential ion/ion reaction method is capable of revealing subtle, but important changes in protein PTMs.

Conventional proteomics approaches rely on the observation of complementary fragment ions. That is, locating fragment ion pairs, e.g., b/y or c/z, whose sum corresponds to the molecular weight of the precursor mass. For a linear ion trap mass spectrometer having a mass range restricted to 2000 m/z, most possible singly charged c and z-type product ions derived from large polypeptide/protein cations would be well beyond this mass range. Nonetheless, because ETD provides extensive backbone cleavage throughout the protein and the charge reduction step ensures all product ions are singly charged, the sequence of the amino and carboxy terminus can be readily identified—even without locating complementary ion pairs. Note that while the higher m/z c and z-type fragments may be produced, they simply are not detected because of the limited mass range of the present linear ion trap mass spectrometer. In another embodiment, the PTR reaction period could be shortened to allow observation of fragment ion charge states greater than 1. This would allow observation of larger mass fragment species that would otherwise be beyond the m/z range of the mass spectrometer.

This mass range limitation will be diminished as mass spectrometer technology advances. First, advances in extending the mass range of the standalone linear ion trap mass spectrometer is expected over the next few years. A mere doubling of the m/z range will roughly correspond to detecting the first and last 30 residues of the protein, as opposed to 15 in the present form. Other hybrid type mass spectrometers are expected to significantly enhance the mass range, and thereby the sequence coverage resulting from the proposed experiment. In this arrangement the linear ion trap mass spectrometer will be utilized to perform the sequential reactions as described above; however, following the reactions the product ions will be sent to a second mass analyzer for m/z analysis. Secondary mass analyzers include, but are not limited to, time-of-flight (TOF), orbitrap, and ion cyclotron resonance (ICR). Use of these secondary analyzers will extend the mass range substantially, and may permit observation of every produced c and z-type ion. Note with higher resolution it may be advantageous to shorten the duration of the PTR reaction so as to allow charge states greater than 1. Obviously, the utility of the experiment will increase as the extent of sequence coverage is extended.

However, there are immediate applications of the sequential ion/ion methodology described herein utilizing the present standalone linear ion trap mass spectrometer. Because the time-scale of this experiment is low, ~500-700 ms/scan, the process is easily performed with chromatography. The experiments described herein provide the first whole protein analysis experiment compatible with chromatographic separation. Complex mixtures of whole proteins can be immediately analyzed in a similar fashion to the polypeptide analysis characterized above. The resulting product ion spectra can be searched against a computer database containing all known proteins. With simple modification of conventional searching algorithms, protein identification will be straightforward.

In accordance with one embodiment determination of the amino- and carboxy-termini in conjunction with the molecular weight of the protein can be used to identify post-translationally modified variants and splice variants of known proteins. More particularly, the original electrospray ionization spectrum affords signals from which one can calculate the molecular weight of the protein. Recently an existing MS-database searching algorithm (OMSSA; Geer et al., Journal of Proteome Research 3 (5): 958-964 SEP-OCT 2004) was adapted to search the whole protein data presented in FIGS. 10, 11, 12, and 14. The program was modified to calculate the first seventeen c and z ions of all proteins (intact) contained in the species-specific non-redundant protein database. The raw data derived from the ETD/PTR sequential reaction for each protein was correlated (separately) to the calculated first 17 c/z ions from all proteins in the database. In all cases, the correct protein was identified with a high probability true positive score. This results confirms the unique ability of ETD/PTR sequential ion/ion reactions, followed by m/z analysis, to rapidly and robustly identify whole proteins.

In one embodiment the resulting product ion spectra will be searched against a database of all known proteins. Each spectrum will contain a series of c-type ions corresponding to the sequence of the amino acids at the amino-terminus of the protein and a series of z-type ions corresponding to the amino acid sequence at the carboxy-terminus of the protein. This information should be sufficient to identify most proteins. The molecular mass of the intact protein will also be known from the m/z values observed in the original electrospray ionization mass spectrum of the precursor. This will be used to confirm the protein identity or to suggest the presence of posttranslational modifications, splice variants, or mutations in the molecule. Use of the above technology should be particularly valuable for characterization of recombinant proteins, including truncated isoforms, employed as drugs or diagnostics in the biotechnology/pharmaceutical industry.

In accordance with one embodiment a method for dissociating multiply charged polypeptide cations is provided. The method comprises the steps of introducing multiply charged cations into an RF electric field ion containment device, introducing gas-phase electron transfer reagent anions into said ion containment device, and mixing the introduced reagent anions so as to facilitate electron transfer from the reagent anions, or derivative reagent ions thereof, to the multiply charged cations. It is considered within the scope of the present invention that the respective cations and/or anion can be directly injected into the RF electric field ion containment device and allowed to mix and react, or alternatively the injected cations and/or anions can be subjected to further manipulations after injection and prior to being mixed together.

In accordance with one embodiment, after the cations are injected into the RF electric field ion containment device, the cations are subjected to one or more of the following manipulations. The this initial cation population may be subjected to m/z isolation, proton transfer charge reduction (including ion parking), photo-dissociation, collisional activation and ion-molecule reactions to produce derivative multiply charged cations of the original injected cation population. Similarly, the originally injected anions can be subjected to various manipulations before the anion is mixed with the cation (or cation derivatives). In particular, the anion population may be subjected to one or more of the following manipulations: m/z isolation, photo-dissociation, collisional activation and ion-molecule reactions to produce derivative singly or multiply charged anions of the original injected anions population.

Accordingly, in one embodiment multiply charged polypeptide cations are injected into an RF electric field ion containment device, gas-phase electron transfer reagent anions are introduced into the ion containment device, the injected anions and polypeptide cation are then optionally further manipulated and then the introduced reagent anions, or derivative reagent ions thereof, are mixed with the multiply charge polypeptide cations, or derivative multiply charged polypeptide cations thereof, so as to facilitate electron transfer from the reagent anions, or derivative reagent ions thereof, to the multiply charge polypeptide cations, or derivative multiply charged polypeptide cations thereof, to produce dissociation product polypeptide cations.

In accordance with one embodiment the kinetic energies of the introduced reagent anions, or derivative reagent ions thereof, and the multiply charge polypeptides, or derivative multiply charged polypeptides thereof, are less than 1 electron volt. In accordance with one embodiment collisions with background gas molecules in the ion containment device are used to reduce the kinetic energies of the anions and the multiply charged cations to near thermal levels during the mixing and reaction step.

In accordance with one embodiment the RF electric field ion containment device is an RF ion guide. In another embodiment the RF electric field ion containment device is an RF ion trap. One such device suitable for use in the present invention is a RF linear multipole ion trap, and in one embodiment the RF ion trap is a RF 3 dimensional multipole ion trap. In one embodiment the anions are injected along the linear axis of a RF linear multipole ion trap.

In accordance with one embodiment a positively multi-charged polypeptide is fragmented using ETD by introducing positively multi-charged polypeptide into an ion trap, introducing gas-phase anions into an ion trap, and mixing the gas-phase anions and the positively multi-charged polypeptide so as to facilitate electron transfer from the radical anions to the positively multi-charged polypeptide, thus inducing fragmentation of the positively multi-charged polypeptide to produce electron transfer dissociation product ions. As used herein the term introducing ions into the ion trap is intended to encompass not only those ions that are directly injected into the ion trap, but also derivative ions that are produced from the originally injected ions after they are injected into the ion trap. The ion trap may be selected from any of the ion containment devices known to those skilled in the art. Suitable devices include Fourier transform ion cyclotron resonance (FTICR) mass spectrometers, RF 3D multipole ion traps (QIT) and RF linear 2D multipole ion traps. In one embodiment the device is selected based on its capability of separately storing anions/cations and subsequently combining them. In one embodiment the ion trap is an RF ion trap, and more particularly, in one embodiment the RF ion trap is a segmented linear RF multipole ion trap.

During or after the mixing of the multiply charged polypeptide and the anion, the electron transfer dissociation product ions can be subjected to additional activation energy. More particularly, the electron transfer dissociation product ions are supplied with sufficient energy to trigger an electron transfer-type dissociation pathway, without production of substantial conventional collision-activated dissociation products. In accordance with one embodiment the procedure produces less than 20% CAD product, in a further embodiment less than about 10% CAD products are produce and in a further embodiment less than about 5% CAD products are produced and in a further embodiment less than about 1%

CAD products are produced. The energy can be supplied in the form of photoactivation or collisional activation. In one embodiment the electron transfer dissociation product ions are subjected to low-energy, off-resonance collisional activation wherein less than 20% of the products produced are conventional collision-activated dissociation products. In accordance with one embodiment the electron transfer dissociation product ions are further activated, after the multiply charged polypeptide have been mixed with the anions, using reduced Finnigan LTQ CAD conditions, having a $q=0.15$ or less, and a normalized activation energy 20% or less, for 60 ms duration). In one embodiment the reduced activation conditions comprise a q value of 0.13 or less, and a normalized activation energy of 17%, for 60 ms duration.

In accordance with one embodiment after the multiply charged polypeptide is mixed with the anion and electron transfer dissociation product ions are formed, the remaining anions from the linear ion trap are ejected, while the electron transfer dissociation product ions are retained within the linear ion trap. The remaining electron transfer dissociation product ions are then subjected to low-energy, off-resonance collisional activation that is insufficient to produce less than about 20% or less than about 5% of total ion products) conventional collision-activated dissociation products.

The electron transfer dissociation product ions produced by the electron dissociation method are then further contacted with a second type anion that will substantially exclusively remove protons from the electron transfer dissociation products and thus reduce the charge of the dissociation products. In one embodiment the first electron transfer anion is expelled from the ion trap and an anions of a second type are then introduced into the linear ion trap and allowed to mix with the dissociation products. In accordance with one embodiment the second anion type is derived from a carboxylic acid, phenolic, and alkoxide containing compound. In one embodiment the second anion is an anion of a compound selected from the group consisting of benzoic acid, PDCH, $SF_6$, and PFTBA.

The present disclosure should not be construed to be limited solely to the assays and methods described herein, but should be construed to include other methods and assays as well. One of skill in the art will know that other assays and methods are available to perform the procedures described herein.

In accordance with another embodiment, ion-ion reactions involving the transfer (abstraction) of electrons from multiply charged polypeptide ions are used to effect negative electron transfer dissociation (NETD) of the polypeptide analyte ions within an RF electric field ion containment device. In the ETD process, the multiply charged polypeptide analyte ions are cations (positive ions). In the NETD process, the multiply charged polypeptide analyte ions are anions (negative ions). The term negative electron transfer dissociation (NETD) is used to distinguish from ETD. ETD and NETD represent two separate and distinct types of dissociation promoting ion-ion reactions, as is suggested by both opposing polarity of analyte ions involved as well as the opposing directions of the electron transfer relative to the analyte. These different processes lead to the dissociation of different chemical bonds along the backbone the analyte polypeptide ions.

In accordance with one embodiment amino- and carboxy terminal sequences are determined for large polypeptides by conducting NETD followed by introducing gas-phase proton donor reagent cations into a ion containment device, mixing the introduced proton donor reagent cations, or derivative proton donor reagent cations thereof, and the dissociation product anions, so as to facilitate proton transfer to said dissociation product anions from the proton donor reagent cations, or derivative proton donor reagent cations thereof, to reduce the charge on the multiply charged dissociation product cations so the remaining charged c and z-type fragments consist essentially of fragments having four or fewer unit charges and then mass (m/z) analyzing the remaining charged fragments and determining amino and carboxy sequences of the polypeptide. In accordance with one embodiment the NETD-inducing cations are removed and replaced with a second set of cations that are capable of charge reduction (10-250 ms) of the dissociation product anion fragments. The purpose of that reaction is to remove the excess charge from the multiply charged fragments. The duration of the second ion/ion reaction is adjusted so that upon completion essentially only low unit charged (e.g., less 4 unit charged, and in one embodiment, singly charged a and x-type fragments remain). Finally, the second cation is removed and an m/z analysis of the resulting c and z-type ions is performed. The generated mass spectrum then contains a c and z-series of fragment ions. Subtraction of neighboring ions in the a series allows one to deduce the sequence of the protein amino terminus; likewise, subtraction of ions in the x series allows sequence analysis of the carboxy terminus.

In accordance with one embodiment ETD can be used for the direct sequence analysis of intact proteins through the use of sequential ion/ion reactions coupled with online chromatography. In this embodiment multiply charged polypeptides are first isolated and reacted with a singly or multiply charged anion within a linear ion trap spectrometer. In one embodiment the anion is a radical anion, and in another embodiment the anion is a singly charged radical anion. After a relatively short reaction (about 5 to about 20 ms) the remaining anions are expelled from the ion trap and the polypeptide ion products are reacted with a second anion injected into the ion trap. The second anion injected into the trap is selected based on its ability to accept protons. The transfer of a proton from the polypeptide ion products serves to simplify the product spectrum to contain only singly protonated fragment ions and to produce a homologous series of singly charged c and z type fragment ions characteristic of the amino and carboxy terminal sequence of the precursor protein. In one embodiment the second anion injected into the ion trap is an even electron anion of benzoic acid and the reaction is conducted for about 75 to about 150 ms.

The present disclosure demonstrates a new method for rapid amino- and carboxy-terminal sequence analysis of intact proteins or large protein degradation products using mass spectrometry and multiple ion/ion reactions. In one embodiment of this arrangement, the intact protein is ionized via electrospray ionization, a process that generally results in the formation of a highly-charged intact protein ion. Multiply charged protein ions are accumulated in a linear ion trap mass spectrometer and subjected to an ion/ion reaction with a selected anion that is capable of inducing electron transfer dissociation. That reaction proceeds rapidly (5-50 ms) and causes extensive fragmentation of the peptide backbone—along with concomitant formation of highly charged c and z-type fragment ions.

Upon completion of the first ion/ion reaction, the ETD-inducing anions are removed and replaced with a second set of anions that are capable of charge reduction (10-250 ms). The purpose of that reaction is to remove the excess charge from the multiply charged fragments. The duration of the second ion/ion reaction is adjusted so that upon completion only singly charged c and z-type fragments remain. Finally, the second anion is removed and an m/z analysis of the resulting c and z-type ions is performed. The generated mass spectrum then contains a c and z-series of fragment ions.

Subtraction of neighboring ions in the c series allows one to deduce the sequence of the protein amino terminus; likewise, subtraction of ions in the z series allows sequence analysis of the carboxy terminus.

In conjunction with the amino and carboxy termini sequence information, the molecular weight of the target polypeptide can also be determined through mass spectrometer analysis and used to help identify an unknown polypeptide present in a sample. The molecular weight can be established using mass spectrometer techniques known to those skilled in the art including, for example, electrospray ionization (ESI), and matrix assisted laser desorption ionization (MALDI). In one embodiment the molecular weight of the intact protein is determined from the m/z values associated different charge states of the same polypeptide species observed in an electrospray ionization mass spectrum.

In accordance with one embodiment a method of randomly fragmenting peptides within a mass spectrometer comprises the following steps:

Gas phase anions are generated from low electron affinity substrates by vaporizing inorganic and organic molecules into a Townsend discharge source or into conventional negative ion chemical ionization source operated with a buffer gas such as methane, isobutane, or argon. These sources produce an abundance of thermal electrons for capture by gas-phase organic or inorganic molecules.

The desired anion will then be injected into an ion storage device in a manner that eliminates or minimizes destruction of the anion by electron detachment. In one embodiment, this step involves injection of anions into the segmented, Thermo Electron, 2D-quadrupole linear ion trap (LTQ) along the linear axis of the device and storage of the ions in segment two of the device. Energetic collisions with the helium bath gas are minimized by this protocol. Accordingly, this procedure makes it possible to employ anions for ETD from substrates having a wide spectrum of electron affinities.

Multiply charged peptide ions will be generated by electrospray ionization and injected into an ion storage device for reaction with negative ions. In one embodiment, this step involves injection of multiply charged positive ions into the segmented, 2D-quadrupole linear ion trap along the linear axis of the device and storage of the ions in the front section of the device.

The two ion populations will be mixed in the center section so as to facilitate electron transfer from the anions to the multiply charged positive ions. Electron transfer from a radical to a positively charged sample ion is sufficiently exothermic to cause fragmentation of the sample polypeptide. The remaining anions are expelled from the ion trap and the polypeptide ion products are reacted with a second anion injected into the ion trap. The second anion injected into the trap is selected based on its ability to abstract protons from multiply protonated polypeptide cations. The transfer of a proton from the polypeptide ion products serves to simplify the product spectrum to contain only singly protonated fragment ions and to produce a homologous series of singly charged c and z type fragment ions characteristic of the amino- and carboxy-terminal sequence of the precursor protein.

Reagent Anions

As noted above, any molecule that possesses a positive electron affinity (EA) (reacts exothermically to form a stable or transiently stable radical anion) can function as an electron donor and thus has the potential to be used a reagent in the electron transfer dissociation reaction. In addition, we have also identified several compounds that form even-electron species that, when reacted with multiply charged peptides, transfer an electron and perform ETD. Thus, formation of a radical anion, is not the sole criteria for determine whether an anion will have electron transfer capacity. Our original studies utilized anions derived from several compounds: FC-43 (perfluorotributylamine, PFTBA), sulfur hexafluoride ($SF_6$), perfluoro-1,3-dimethylcyclohexane (PDCH), hexafluorobenzene ($C_6F_6$). In this work ETD-type fragmentation were observed, but predominately the proton transfer reaction occurred. Then we initiated the ability to isolate a specific anion species for reaction with a selected peptide ion. At that time, we discovered that background ions, not the above described species were responsible for the low-level ETD fragmentation. Isolation of the anions from both sulfur hexafloride and PDCH demonstrated that those anions solely induced proton transfer reactions and no detectable ETD was observed.

Aromatic species such as anthracene, which is converted to $C_{14}H_{10}^{\bullet-}$ were then investigated as the reagent. To minimize proton transfer to the anion, the use of 9,10-diphenylanthracene as a reagent can also be used. Additional aromatic compounds used as anions for promoting electron transfer dissociation include aromatic hydrocarbons (multi-cyclic aryls) and substituted aromatic hydrocarbons. In accordance with one embodiment a polyaromatic hydrocarbon having the general structure:

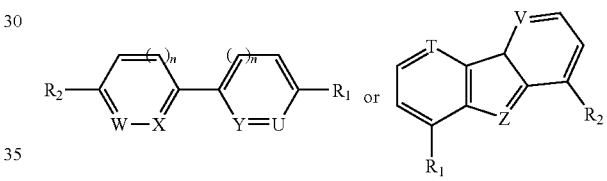

wherein n is 1 or 0;

X is selected from the group consisting of S, O, N, NH, $CR_5$, and $CHR_5$;

Y is selected from the group consisting of S, O, N, NH, $CR_6$, and $CHR_6$;

W is selected from the group consisting of S, O, N, NH, $CR_7$, and $CHR_7$;

U is selected from the group consisting of S, O, N, NH, $CR_8$, and $CHR_8$;

Z is selected from the group consisting of S, O, N, NH, $CR_3$, $CHR_3$ and —$CHR_8CHR_7$—, T and V are independently selected from the group consisting of S, O, N, NH, $CR_4$, and $CHR_4$; wherein $R_1$, $R_2$, $R_3$, $R_4$, $R_5$ $R_6$, $R_7$ and $R_8$ are independently selected from the group consisting of H, $C_5$-$C_6$ aryl, $C_5$-$C_6$ heteroaryl, halo, CN, $C_1$-$C_4$ alkyl, amino and hydroxy, or $R_1$ and $R_8$, and/or $R_2$ and $R_7$, together with the atoms to which they are bound form a $C_5$-$C_6$ aryl, $C_5$-$C_6$ heteroaryl ring or $R_7$ and $R_5$, and/or $R_6$ and $R_8$ together with the atoms to which they are bound form a $C_5$-$C_6$ aryl, $C_5$-$C_6$ heteroaryl ring or $R_2$ and $R_3$, together with the atoms to which they are bound form a $C_5$-$C_6$ aryl, $C_5$-$C_6$ heteroaryl ring.

In accordance with one embodiment, n is 1, X and Y are independently selected from the group consisting of S, O, N, NH, CH, and $CH_2$; W is $CR_7$, or $CHR_7$ and U is $CR_8$, and $CHR_8$, wherein $R_7$ and $R_8$ are independently selected from the group consisting of H, $C_5$-$C_6$ aryl, $C_5$-$C_6$ heteroaryl or $R_1$ and $R_8$, together with the atoms to which they are bound form a $C_5$-$C_6$ aryl, $C_5$-$C_6$ heteroaryl ring, and $R_2$ and $R_7$, together with the atoms to which they are bound form a $C_5$-$C_6$ aryl, $C_5$-$C_6$ heteroaryl ring. In another embodiment T and V are independently selected from the group consisting of S, O, N, NH, $CH_2$, and CH, Z is selected from the group consisting of S, O, N, NH, CH and $CH_2$ and $R_1$ and $R_2$ are independently selected from the group consisting of H, $C_5$-$C_6$ aryl, $C_5$-$C_6$ heteroaryl, halo, CN, $C_1$-$C_4$ alkyl, amino and hydroxyl. In another embodiment T and V are independently selected from the group consisting of S, O, N, NH, $CH_2$, and CH, $R_1$ is H, and Z is $CHR_3$, wherein $R_2$ and $R_3$, together with the atoms to which they are bound form a $C_5$-$C_6$ aryl, $C_5$-$C_6$ heteroaryl ring. In another embodiment, T and V are independently selected from the group consisting of S, O, N, NH, $CH_2$, and CH, and Z is —$CHR_8CHR_7$—, wherein $R_1$ and $R_9$, together with the atoms to which they are bound form a $C_5$-$C_6$ aryl, $C_5$-$C_6$ heteroaryl ring, and $R_2$ and $R_7$, together with the atoms to which they are bound form a $C_5$-$C_6$ aryl, $C_5$-$C_6$ heteroaryl ring.

All aromatic hydrocarbons tested have some ability to induce electron transfer dissociation when reacted with multiply charged peptides. Tested anions include napthalene, fluorene, phenanthrene, pyrene, fluoranthene, chrysene, triphenylene, perylene, acridine, 2,2' dipyridyl, 2,2' biquinoline, 9-anthracenecarbonitrile, dibenzothiophene, 1,10'-phenanthroline, 9' anthracenecarbonitrile, and anthraquinone. Anions derived from all of these compounds induced electron transfer dissociation to some extent. While all of these aromatic hydrocarbons promote electron transfer, fluoranthene works particularly well as does 2,2' biguinoyline and azuline. The chemical structures of several of the compounds tested for their ETD-inducing ability are as follows:

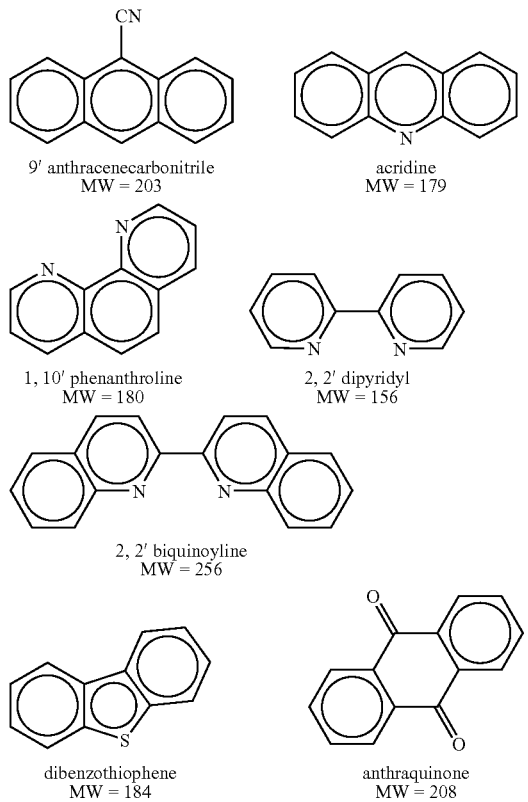

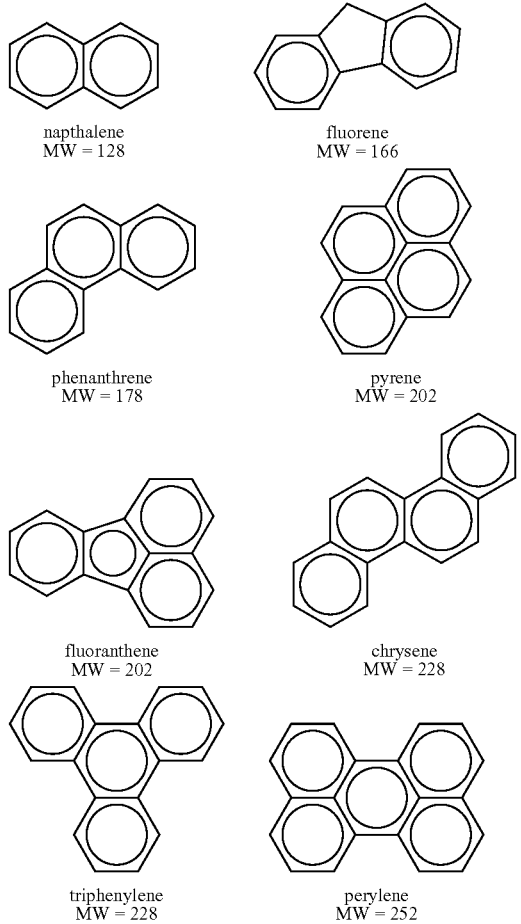

Therefore, aromatic hydrocarbon compounds when converted to their respective anions, represent one general class of compounds that will transfer electrons to a multiply charged cation. Further, modification of these compounds to include atom(s) of sulfur, oxygen, or nitrogen (heterocyclics) should not alter their electron transfer capability and are therefore are to be included in this group electron transfer promoting compounds. Accordingly, in one embodiment of the present invention, multi-cyclic aryl and heteraryl compounds are used as anions for promoting electron transfer dissociation of polypeptides in accordance with the present invention. Table 1 presents the compound, molecular weight, and the observed m/z of its corresponding anion(s).

TABLE 1

| compound | molecular weight | anion m/z |
|---|---|---|
| napthalene | 128 | 127, 128, 129 |
| fluorene | 166 | 165, 166, 180 |
| phenanthrene | 202 | 177, 178 |
| pyrene | 202 | 201, 202 |
| fluoranthene | 202 | 202 |
| chrysene | 228 | 227, 228, 229 |
| triphenylene | 228 | 227, 228, 229 |
| perylene | 252 | 252 |
| 9' anthracenecarbonitrile | 203 | 202, 203 |
| acridine | 179 | 178, 179 |
| 1,10' phenanthroline | 180 | 179, 180 |
| 2,2' dipyridyl | 156 | 155, 156 |

TABLE 1-continued

| compound | molecular weight | anion m/z |
|---|---|---|
| 2,2' biquinoyline | 256 | 256 |
| dibenzothiophene | 184 | 183, 184 |
| anthraquinone | 208 | 207, 208 |

Instrumentation

In accordance with one embodiment the instrument used to perform these experiments is a commercially available system that is modified to perform the steps required for an improved method of fragmenting peptides in a 2-D-multipole ion trap, a modified Finnigan LTQ (Thermo Electron Corp.). Other alternative apparatus configurations may be used incorporating other commercially available or custom-made components. The ion path mechanics or applied voltages for the ion path components between the ESI source to the RF QLT were not altered. Briefly, the Finnigan LTQ 2-D-multipole ion trap was modified as follows. A fifth differentially pumped vacuum region was attached to the rear vacuum flange of the instrument to accommodate a Finnigan MAT 4500 ion source. This region is pumped with the high vacuum stage of a dual stage turbo-molecular pump, Pfeiffer model TMH 230-160 backed Alcatel 2008A-rotary vane mechanical pump. Two RF octopole ion guides, labeled Rear Octopole #1 and Rear Octopole #2, were used to transport ions emanating from the Finnigan MAT 4500 ion source. The aperture of the plate lens (Rear Inter-Octopole Lens) which separates the two RF octopole ion guides, serves as the differential pumping conductance limit between the added vacuum stage, Vacuum region #5 and the vacuum region of the LTQ containing the RF linear quadrupole ion trap, QLT. Rear Octopole #1 is composed of a pair of 2 inch long octopole electrode assemblies ($r_0$=0.108 in.), from a Finnigan LCQ placed end to end and electrically connected as one unit. Rear Octopole #2 is simply a single LCQ octopole electrode assembly. The RF QLT assembly was not mechanically modified. However the electrical connections of the Front Lens and Back Lens electrodes have been changed to enable superposition of a RF voltage on to the DC bias voltages for theses lenses provided by the standard electronics.

The ion source lens voltages are supplied by a Finnigan MAT 4500 PPNICI Control Module and the filament power and emission control is supplied by a Finnigan MAT 4600 Quadrupole Electronics Module (QEM). Source heater power and regulation is provided by a home built unit based on a Omega Model CN9000A temperature controller and a 1.5 A 24VAC transformer. The source calibration gas solenoid valve is operated by another homebuilt unit. The source's standard probe vacuum interlock bellows valve has been replaced with a ball valve [A and N Corporation]. Provision is made for the rough evacuation of the probe interlock and the calibration gas inlet with a set of toggle valves and Alcatel Model 2012 mechanical pump.

The rear octopole RF and DC voltages as well as the RF voltage for the QLT end lenses are provided by home build electronics modules which use modified circuitry from Finnigan LCQ and TSQ 7000 instruments. Both octopoles are driven with the same RF voltages though they have separate DC bias voltages. Similarly the QLT end lenses receive the same secondary RF voltage but have separate DC bias voltages. Two frequency synthesizers, Wavetek/Rockland Model 5100 and Stanford Research Systems Model_DS340, provide, respectively, the reference frequencies for the octopole and end lens RF electronics. The amplitudes of both the rear octopole and end lens RF voltages are controlled by spare DACs (Digital to Analog Converters) in the LTQ electronics. The instrument's embedded computer control system was reconfigured to enable control of these voltages during the execution of mass spectral experiments (scan functions).

When operated in the negative chemical ionization mode, the ion source lenses, L1, L2 and L3 (where L1 is the lens closest to the ion volume and L3 is the farthest) have DC bias voltages of +10V, +70V and +23V respectively. For transmission of anions to the QLT, the RF voltage between adjacent rods is typically about 300 Volts zero-to-peak at a frequency of about 2.2 MHz. The rear octopole RF amplitude is made zero when the anion transmission to the QLT is to be interrupted (gated off).

The standard nano-flow ESI source was used for the instrument. For most of the work, mixtures of standard peptides in 40% aqueous acetonitrile w/0.1% acetic acid were infused at 100 nl/min. The source was used without modification. For the LC/MS experiments, the source had to modified to appropriately mount and electrically connect to the homemade packed capillary HPLC columns with integral laser pulled electrospray emitters that we use in our laboratory.

The computer programs that govern the control of mass spectrometer to perform the ETD MS/MS experiment were modified. The operation of radial ejection RF quadrupole linear traps has been described in detail in Schwartz et. al. (J. Am. Soc. Mass Spectrom. 2002, 13, 659-669). The instrument described in that article is the direct precursor to the Finnigan LTQ.

Operating Procedure

Multiply charged peptide cations were generated by electrospray ionization (ESI). A 40% aqueous acetonitrile solution (with 0.1% acetic acid), containing peptides at 1 µmol/µL, was infused into a SilicaTip™ fused silica emitter (30 µm tip, New Objective, Woburn, Mass., USA). Peptides studied include adrenocorticotropic hormone fragment 1-24 (ATCH hormone, Sigma-Aldrich, St. Louis, Mo., USA), and an in-house synthesized phosphopeptide. Negative chemical ionization, with methane buffer gas (MG Industries, Malvern, Pa., USA), was used to produce anions of $SF_6$ (MG Industries, Malvern, Pa., USA) and PDCH (Sigma-Aldrich, St. Louis, Mo., USA). A Finnigan LTQ linear ion trap mass spectrometer (ThermoElectron, San Jose, Calif., USA) was adapted to accept a Finnigan 4500 chemical ionization source (Finnigan, Sunnyvale, Calif., USA), which was mounted on the rear side of the device—opposing the factory nanospray source. The sequence of scan events includes: precursor ion isolation (within the linear quadrupole ion trap), introduction of anions for ion/ion reactions, and finally mass analysis of the product ions as describe in more detail as follows:

1. Injection of Cations Generated by the ESI Source into the Quadrupole Linear Trap (QLT) where they are Collisionally Stabilized and Trapped.

The skimmer electrode of the atmospheric pressure interface is maintained at ground potential, 0 volts, thus the cations entering the QLT have essentially zero kinetic energy at 0 volts. Hence biasing the Back Lens electrodes at ground potential, raises that DC axis potential so that injected ions which have undergone a few dissipative collisions with the background are reflected back toward the front of the device. Injected ions undergo many further momentum depleting collisions with the Helium (about 3 mTorr) atoms efficiently damping their axial motion and causing them to be trapped in the axial DC well created by the low bias potential of the Center Section of the device. These collisions also damp the radial motion of the ions such that ions, under the influence of the radial strong focusing effect of the RF quadrupole field, relax to the vicinity of the central axis of the device. Unless subjected to further kinetic excitation, collisions with Helium will reduce the kinetic and internal energies of the trapped cations to near thermal levels within about 1-2 msec. Fully collisionally relaxed trapped ions will remain confined to within about 1.0 mm of the central axis.

Generally, to avoid space charge effects that interfere with the proper performance of the QLT, it is desirable to prevent accumulation of ions of mass-to-charge ratios other than those within the desired precursor m/z range. This is accomplished by superposing a supplementary dipolar broadband AC field on to the RF quadrupole trapping field to resonantly eject ions of which have characteristic frequencies of motion in the quadrupole field (motion transverse to the device's axis) that deviate from those of ions within the precursor m/z window. The optimal intensity of the RF quadrupole field for the injection and accumulation of precursor ions does not allow efficient accumulation of precursor ions and achievement of a m/z isolation band of about 3 Th (Daltons/unit charge) or less that is generally required. So "injection waveform" isolations are, by necessity, rather coarse, typically, only preventing the accumulation of ions with m/z ratios outside of about ±2-10% of the precursor m/z ratio.

2. Precursor m/z Isolation.

Within a few milliseconds after termination of cation injection and cessation of any application of an "injection waveform" field, the intensity of the RF quadrupole trapping field may be increased such that ion isolation may be effected with the desired m/z resolution and high efficiency (lowest loss of precursor ions). A higher resolution "waveform" field is applied so that all cations outside of the desired precursor m/z window are resonantly ejected from the QLT. Normally more than 90% of the precursor ions are retained. During m/z isolation, the DC bias potentials of the Front Section and Back Section of the QLT are maintained at about +12 volts relative to the Center section to confine the cations within the Center Section of the device.

3. Relocation of Precursor Cations to the Front Section of the QLT.

After precursor m/z isolation is complete, the DC bias potential of the Front Section is reduced to 1 volt below that of the Center Section. The Front lens DC bias is maintained above both those of the Center Section and Front Section to maintain axial confinement of the Cations. Within a few milliseconds, all of precursor ions initially in the Center Section diffuse to the Front Section, where again, damping collisions with Helium atoms cause them to remain.

4. Injection of Anions Generated by the NICI Source into the QLT where they are Collisionally Stabilized and Trapped in the Center Section of the Device.

Once the precursor ions have been moved to the Front Section, the DC bias potentials of the Center Section, Back Section and Back Lens are elevated above "ground" potential to permit injection and trapping of the anions. The NICI source is biased at 0 volts so maintaining the Front Section at a negative DC bias voltage both maintains trapping of the precursor cations, and creates an axial potential barrier at the front of the device for the negative ions. The DC bias of the Center Section is made more positive then that of the Rear Section so that in the anions accumulate in this section of the device. This step corresponds to the injection and accumulation of cations in Step 1, except that the anions are injected from the back end of the device and, because anions are by definition negatively charged, the DC bias potentials have opposite signs.

During anion injection it is technically feasible to apply an "injection waveform" to resonantly eject anions which have neither m/z ratios close to that of the desired reagent anions nor m/z ratios close to those of the previously selected precursor cations. However, we suspect that the kinds of anions that are most likely to promote ECD will readily undergo electron detachment if they are subjected to even modestly energetic collisions. Thus any extra kinetic excitation of the reagent anions beyond that associated with ion injection might cause loss of the very anions that we wish to isolate. So reagent anion isolation during injection may be undesirable. The typical duration for anion injection is anywhere from 1 ms to 1 sec. (ideally just a few milli-seconds) depending upon the anion current provided by the NICI source.

5. Reagent Anion m/z Isolation or m/z Elimination.

Within a few milliseconds after termination of anion injection, the intensity of the RF quadrupole trapping field may be adjusted such that isolation of the precursor may be effected with the best attainable m/z resolution and efficiency. As mentioned above, the anion isolation "waveform" must resonantly eject anions which have neither m/z ratios close to those of the desired reagent anions nor close to the m/z rations of the previously selected precursor cations. Thus undesired anions of m/z ratios close to that of the selected precursor m/z window will not be ejected. This arrangement is not ideal. However it will require substantial changes in the design of the QLT and/or the voltages that drive it to circumvent this problem. The current implementation does insure that most undesired anions are eliminated from the trap prior to the initiation of cation-anion reactions.

A fundamental attribute of ion motion in an RF-only quadrupole trapping field is that at any particular intensity of the RF quadrupole trapping field, there is a corresponding threshold m/z ratio (which is proportional to the intensity of the field) for ion trapping. Only ions with m/z ratios above this threshold m/z ratio may be trapped. Ions with m/z ratios below this threshold are radially ejected. We have often used the simple manipulation of the magnitude of the RF voltage applied to the QLT electrode to eliminate undesired anions species below the m/z of the reagent anions of interest.

A simple method of determining which anions promote ECD is to resonantly eject a relatively narrow window of m/z, corresponding to a targeted anion species, using a single frequency "waveform" prior to or during the ion-ion reaction step. Such an approach should cause less kinetic activation of the anions retained in the trap thus reducing the probability of anion loss due to electron detachment.

6. Mixing of Precursor Cations And Reagent Anions to Cause Cation-Anion Reactions and the Production of ETD Product Ions.

Once the desired trapped precursor cation and reagent anion populations have been established and have been allowed to collisionally relax, a secondary RF voltage is applied to both the end lens plates of the QLT (According to our nomenclature the RF voltages applied to the QLT electrodes to effect radial containment are primary RF voltages). The effect of this secondary RF potential is to repel both positive and negative ions. For any given m/z this repulsive effect can be modeled as repulsive potential that varies inversely with m/z. and is referred to in the literature as a pseudo-potential or effective potential. To effect simultaneous trapping of both anions and cations in the same region of the QLT, and thus permit cation-anion reactions to occur, the DC bias voltages applied to the trap segments and end lenses are made equal (nominally 0.000 volts). The pseudo-potentials established by the secondary RF voltages applied to the end lenses provide the necessary axial trapping for both the cations and anions.

In all of the work presented here, a secondary RF voltage with an amplitude, $V_2$, of 100 V (0-peak) and a frequency, $f_2$, of about 600 kHz (½ the frequency of the quadrupole field, $f_1$) is applied to both end lenses during the cation-anion reaction interval. It provides efficient simultaneous trapping of ions of both polarities with m/z ratios ranging from below 100 u to beyond 2000 u. The axial pseudo-potentials only have significant action in the close vicinity of the end lenses; so both the anions and cations diffuse throughout all three sections of the device and are free to react. Presently, we are only able set the DC biases of the three sections of the QLT to be equal to within about ±0.030 volts. A single increment of the DACs which control these bias voltages corresponds to a about 0.063 volt change in bias voltage. Since the mean thermal kinetic energy of an ion at 300° C. is about 0.030 eV, these small differences in bias potentials could be causing some axial segregation of the trapped anions and cations. However, as we observe abundant cation-anion reaction products, this doesn't appear to be happening in a gross sense. The trapped ion populations are probably sufficiently high to create a compensating space charge potential in every segment. The ions should distribute themselves to provide a uniform axis potential, thus allowing free movement of ions along the device axis. It is conceivable that the axial mobility of ions could be m/z dependent as lower m/z ions are generally confined closer to the central axis. Therefore it would be preferred if the DC bias potentials of the three segments match within about ±0.001 volts during the cation-anion reaction period. Such bias differences should have negligible anion-cation segregation at laboratory temperature. It may be possible to avoid cation-anion segregation by alternating the sign of the bias differences repetitively so that the trapped ions are constantly forced to axially redistribute and therefore stay mixed.

The larger the reagent anion population, the more rapid the conversion of precursor ions to product ions. With suitably large reagent anion populations, ion-ion reaction periods of 30-100 ms are typically adequate to react most of the precursor cations. For the results shown herein, about 3,000-30,000 precursor ions were typically isolated (this assumes that the precursor species was triply charged, and corresponds to AGC $MS^n$ target values of 10,000-100,000). The initial number of reagent anions available for ion-ion reaction was probably a least about 3-10 fold greater than the initial population of precursor ions. As discussed earlier, the initial number of the reagent anions of types which promote ETD probably varied by orders of magnitude depending upon the compounds that were introduced to the NICI ion source.

The ETD and proton transfer product ions potentially can undergo further reactions with reagent anions. Such secondary reactions will cause neutralization and therefore loss of any singly charged cation products. It also will likely produce second generation product ions which contain neither the amino- nor the carboxy-terminus of the originating precursor peptide cation. Such "internal fragment" product ions are undesirable as they complicate interpretation of the resulting product ion mass spectrum. Methods have been developed for charge reduction (proton transfer) ion-ion experiments in 3D RF quadrupole ion traps to inhibit such secondary reactions (see U.S. Patent Applications Publications Nos. US 2002/0092980 and US 2002/0166958, the disclosures of which are incorporated herein). It is anticipated that these methods can be adapted to inhibit secondary reactions between reagent anions and ETD product cations in 2D RF quadrupole ion traps.

While perhaps undesirable in terms requiring longer reaction times, longer ion accumulation times, and perhaps higher minimum sample levels, using a large ratio of precursor cations to reagent anions would produce fewer secondary product ions. Since the precursor cation population would always be much larger than the product cation population, anions would be much more likely to react with precursor ions than with product ions. It is conceivable that the ratio of precursor ions to reagent ions could be adjusted automatically depending upon the accumulation rate of the precursor (rate of production of precursor ions from the ESI source) thereby reducing the production of secondary product ions when precursor ions are plentiful.

In our present experiments, proton transfer generally produces large numbers of primary and secondary product ions. For example, a quadruply charged precursor ion, $[M+4H]^{4+}$, through a succession of proton transfer reactions, produces triply charged primary product ion, $[M+3H]^{3+}$, as well as doubly charged, $[M+2H]^{2+}$, and singly charged, $[M+H]^+$, secondary product ions. The secondary product ions may have the same m/z ratios as ETD product ions thus interfering with their observation. Continuous resonant ejection of the primary proton transfer product ions during the cation-anion reactions eliminates the production of such interfering secondary proton transfer product ions. This also prevents the production and observation of secondary ETD product ions from primary and secondary proton transfer products. We have successfully demonstrated this procedure though it was not used for the collection of the data shown herein.

After a defined reaction period, the EDT reagent anions are axially ejected, while the cation products are moved back to the front section of the ion trap. Unreacted precursor cations and undissociated products may also be selectively eliminated from the trap (typically via resonant ejection). Then anions are once again injected into the center section of the linear ion trap. This time the ETD reagent anions are selectively removed from the ion trap along with any background anions that are known not to act as PTR reagents, retaining those anions that are proton acceptors (including for example, anions of benzoic acid). The proton transferring ions, initially stored in the center section, are allowed to mix with the c and z-type fragments produced from the prior ETD reaction. After another defined reaction period, the anions are axially ejected and finally an m/z analysis of the c and z-type products is conducted.

7. Termination of Ion-Ion Reactions.

To end the cation-anion reactions, the DC bias voltage of the Center Section is lowered relative to the DC biases of the end sections and the end lenses. Within a couple of milliseconds, all of the cations migrate to the center section and all of the anions migrate to the end sections of the QLT. Then the axial trapping RF voltages (Secondary RF voltage) applied to end lens plates is turned off releasing the anions. For diagnostic purposes it is often useful to obtain a m/z spectrum of the unreacted reagent anions. This can be readily accomplished by terminating the cation-anion reactions by raising the relative DC bias of the Center Section instead of lowering it as described above. This retains the anions in the Center Section and axially extracts the cations.

Prior to mass analyzing the product cations, it may be desirable to eliminate by resonant ejection cations with specific m/z ratios. Likely candidates for elimination would be unreacted precursor ions and proton transfer product ions (charge reduced product ions). Given the currently attainable precursor to ETD product efficiencies of ca 10-20%, a reasonable strategy for obtaining suitable numbers of ETD product ions is to isolate a substantial excess (about 5-10 fold) of the quantity of precursor cations that could be directly m/z analyzed and meet the instrument specifications for m/z assignment accuracy and resolution (spectral space charge limit [25]). However after the cation-anion reaction step, the total number of retained ETD product ions (and more specifically, the total charge of the retained ETD product ions) is within the spectral space charge limit.

Eliminating the excess charge associated with retained unreacted precursor ions and any retained proton transfer product ions enables mass analysis of the ETD product ions with good m/z accuracy, resolution. Since the total charge of the retained ETD product ions is near the spectral space charge limit, the dynamic range of the product ion spectrum the highest that the instrument can provide. This will improve the observation of minor component ETD product ions (i.e., small ETD peaks).

It should be understood that the above procedure is generally performed as part of a greater sequence of experiments. Cation injection times would normally be determined from a prior experiment (or experiments) which allow estimation of the rate of accumulation of precursor cations in the trap during the cation injection step, 1, and a predetermined target amount of total precursor cation charge to be used in the experiment. This approach to the regulation of stored ion charge (space charge) in RF quadrupole ion trap mass spectrometers is known in the art as Automatic Gain Control (AGC).

Implicit in the ordering of the events of the above procedure is the assumption that m/z of the cation precursor is greater than that of the reagent anions. If the reagent anions are to be m/z isolated and have m/z ratios much greater than the specified precursor m/z window it may be desirable to reverse the sequence of cation and anion injection and isolation. The trapping conditions for optimal isolation of the reagent anions may be incompatible with trapping of the lower m/z cations. In this case the anions would be injected first and collected in the Center Section. The reagent anions would be m/z isolated and then relocated the Back Section. Then the cations would be in injected and trapped in the Center Section and the precursor cations would be m/z isolated without causing resonant ejection of the reagent anions. The rest of the experiment would be the same as described above.

The above discussion has focused on implementation of ETD on a RF QLT mass spectrometer. Various mass spectrometer systems which utilize charge sign independent ion trapping in RF multipole linear ion traps for ion-ion type experiments are suited to performing ETD/PTR MS/MS experiments. In one embodiment an RF trap apparatus suitable for performing precursor cation and reagent anion isolations as well as for performing the charge sign independent trapping for the ETD process would be the 6 segment trap. This device would essentially constitute a QLT constructed from a pair of three segment traps (like LTQ device) placed end on end. Such a "dual" three segment trap would allow independent m/z isolation of both the precursor cations and reagent anions. Obviously one of the halves of this "dual" trap could also serve as the scanning m/z analyzer. If m/z selection of the precursor cations and anions is done prior to their injection into the RF quadrupole linear trap, then 2 or 4 segment (depending on if the Secondary RF voltages for axial trapping are applied to the end plate lenses or as dipolar voltages between apposing rods in the end sections) would be quite satisfactory.

Example 1

Use of Anions for Electron Transfer Dissociation of Polypeptides

In accordance with one embodiment FC-43 (perfluorotributylamine, PFTBA), sulfur hexafluoride ($SF_6$), perfluoro-1,3-dimethylcyclohexane (PDCH), hexafluorobenzene ($C_6F_6$), and anthracene were introduced into the NICI (negative ion chemical ionization) source to produce anions for the experiment. In all cases, anions created in the source have produced at least some ETD products when reacted with a standard peptide precursor ion. When FC-43, the standard m/z calibrant used for mass spectrometers with electron impact ionization sources, was introduced to the source a few c and z ions were produced with very low precursor to ETD product conversion efficiency. In subsequent experiments, the above mentioned molecules were introduced into the ion source separately and all produced extensive c and z type fragmentation of our standard precursor ion, a triply charged 12 amino acid phosphopeptide. Precursor to ETD product conversion efficiencies ranged from about 0.1-1% for $SF_6$ and PDCH, about 0.5-5% for ($C_6F_6$) and about 5-20% for anthracene and 9,10 diphenyl-anthracene.

The other source of anions that has produced precursor to ETD product conversion efficiencies nearly as high as those observed with anions derived from anthracene, was the "residual" or "background" gases in the CI ion source. Prior to this experiment increasing the number of precursor ions present when the ion-ion reactions were initiated did not increase the number of ETD product ions (in absolute numbers). This was curious since it was believed that throughout the ion-ion reaction period many more anions were present in the ion trap than there were precursor cations. Furthermore, it was verified at the end of the ion-ion reaction period the anion population was not depleted. Under these conditions, the number of ETD products generated should be nearly proportional to the initial number of precursor cations (first order kinetic theory should apply). Indeed, proton transfer products appeared to be produced in approximate proportion to the initial number of precursor ions. If ETD products were being produced by reactions with a minor component (or components) of the mixture of anions and the minor component of anion was being depleted during the ion-ion reaction period the observations could be explained.

One possibility was that the hypothesized minor component anions were derived from residual background gases (contamination) in the ion source that was responsible for the production of the ETD product ions. In this experiment there were residual amounts of FC-43, $SF_6$, PDCH, and $C_6F_6$ as well as various unknown background compounds which produced ions by electron capture in the CI ion source and were used as the reagent anions. When an abundant reagent anion population derived from "background" compounds was used, the number of ETD product ions produced became proportional to the initial number of reagent ions. The precursor to ETD product efficiency of the experiment also improved substantially.

The procedure was modified to allow for the ability to resonantly eject a selected narrow m/z range of ions from the ion trap, and thus include or exclude a specific reagent ion species from being present during the ion-ion reaction period.

The facility of prominent reagent anions derived from ion source "background" compounds to produce ETD products was probed in this manner. The exclusion of a reagent anion species having m/z 181 (mono-isotopic m/z) during the ion-ion reaction period reduced the production of ETD products by a factor of about 3-5 relative to that of the proton transfer products which were not substantially reduced. This species is believed to be $C_6F_5CH_2-$, formed by an ion molecule reaction between $C_6F_6^{\bullet-}$ and methane, $CH_4$, in the NICI ion source. In addition the reagent anions derived from anthracene (via ion molecule reactions of $C_{14}H_{10}^{\bullet-}$ and $CH_4$), also promote ETD. When anthracene is introduced to the NICI source to produce these reagent anions, ETD product ions are produced in proportion to the initial number of precursor cations. Variations in the ratio of proton transfer to ETD products, with changes in the RF voltages applied to QLT during the ion-ion reaction period, was also observed.

Example 2

Sequential Ion/Ion Reactions

As described above, certain anions act primarily as either ETD or PTR reagents. By exposing cations to anions from either category, these discrete reactions can be performed separately and successively. For example, highly charged peptide precursor ions (e.g., z>4) can be dissociated using ETD-inducing anions followed by removal of those reagents and introduction of a second, PTR-inducing anion type. The duration of this second reaction can be adjusted so that charge-states of the product species are reduced in a controlled manner. That is, a +10 precursor peptide could be dissociated via ETD to yield fragments having charges ranging from +1-+9. Of course, m/z resolution of isotopic peaks of such highly charged products can be problematic; therefore, the second PTR reaction duration can be adjusted so that the ETD products are converted to primarily the +1 charge-state. The net effect is to convert ETD fragments, initially produced in a variety of charge states, to lower charge states and, thus, simplifying spectral interpretation. Such procedures allow for the simultaneous mass analysis of the singly charged ETD products to simultaneously determine the carboxy and amino terminal amino acid sequence of the polypeptide.

Obviously, other sequences or successions of ETD and PTR have utility, either alone or in tandem, with other ion manipulation methods (e.g., activation or m/z selection). In some instances it may be advantageous to charge reduce cation precursors prior to ETD or other ion manipulation techniques.

Methods:

A Finnigan LTQ linear ion trap mass spectrometer was adapted to accept a chemical ionization source mounted on the rear side of the device, opposing a factory nanospray source peptide ion production. Negative chemical ionization (methane buffer) was used to produce anions of fluoranthene, benzoic acid, and sulfur hexafluoride. Introduction of fluoranthene and benzoic acid was accomplished via a batch inlet consisting of a gas chromatograph oven and a heated transfer line. Sulfur hexafluoride was introduced through a leak valve directly into the source (it is a gas). For charge-sign-independent trapping the LTQ electronics were modified to allow superposition of a secondary RF trapping voltage to the end lenses of the QLT.

Results:

Using a modified linear ion trap mass spectrometer, we demonstrate direct interrogation of highly charged peptides using sequential ion/ion reactions. Here the +7 ACTH peptide (SYSMEHFRWGKPVGKKRRPVRVYP$^{7+}$; SEQ ID NO: 4) (m/z 420) was first isolated and then reacted with the anion of fluoranthene for a duration of ~75 ms (ETD). The spectrum produced following this reaction is shown in FIG. 7). The peptide is dissociated at most backbone bonds; however, many of the fragments have charges that are beyond the resolving power of the mass spectrometer used here (see inset, m/z's marked with a dot). To avoid this problem, we have implemented a sequential ion/ion reaction. In this experiment, following the ETD reaction, and the expulsion of excess fluoranthene anions, the resulting multiply charged product ions are reacted with even anions of sulfur hexafluoride (200 ms). This second reaction (proton transfer, PTR) serves to simplify the product spectrum to contain only singly protonated fragment ions and to concentrate the various c and z-type product ion signals into one charge state. The net result is the production of a homologous series of singly charged c and z-type fragment ions characteristic of the amino- and carboxy-terminal sequence of the precursor peptide (the linear trap has a limited m/z range of 2000). Note elimination of the multiply charged fragments denoted in the upper inset.

In FIGS. 8A & 8B, the same experiment was performed, only this time utilizing benzoic acid as the PTR anion rather than sulfur hexafluoride. Note we have also reduced the duration of the initial ETD reaction. Again, the multiply charged fragment ions generated following the ETD experiment are charge reduced and concentrated to predominately the +1 charge state after the second PTR reaction. As the reaction period is extended, the higher-charged fragments are preferentially concentrated to lower charge states—predominately singly charged products in the case of the 150 ms reaction with benzoic acid (FIG. 8B). Obviously higher mass c and z-type fragment ions are produced following the ETD reaction, unfortunately the simplifying proton transfer reaction increases their m/z values beyond our limited mass range. Coverage can be extended by choosing a PTR reaction time to yield mostly doubly and singly charged fragment ions, which are compatible the upper limit of the instrument's m/z resolving power. The PTR reaction duration can be adjusted to produce product charge-states commensurate with the mass analyzer m/z resolving power. Alternatively, hybridization of this ion/ion device with other mass analyzers will also extend this mass range limitation (e.g., TOF, ICR-MS, orbitrap, etc.).

Example 3

Use of Aromatic Hydrocarbon Anions to Promote Electron Transfer Dissociation

Anions that promote electron transfer dissociation have been investigated. Many of these anions belong to a class of compounds referred to as aromatic hydrocarbons. Our results demonstrate virtually all aromatic hydrocarbons tested have some ability to induce electron transfer dissociation when reacted with multiply charged peptides. The anions tested include napthalene, fluorene, phenanthrene, pyrene, fluoranthene, chrysene, triphenylene, perylene, acridine, 2,2' dipyridyl, 2,2' biquinoyline, 9' anthracenecarbonitrile, dibenzothiophene, 1, 10' phenanthroline, and anthraquinone. While all of these aromatic hydrocarbons promote electron transfer, both fluoranthene and 2,2' biquinoyline work particularly well.

Figure 9:
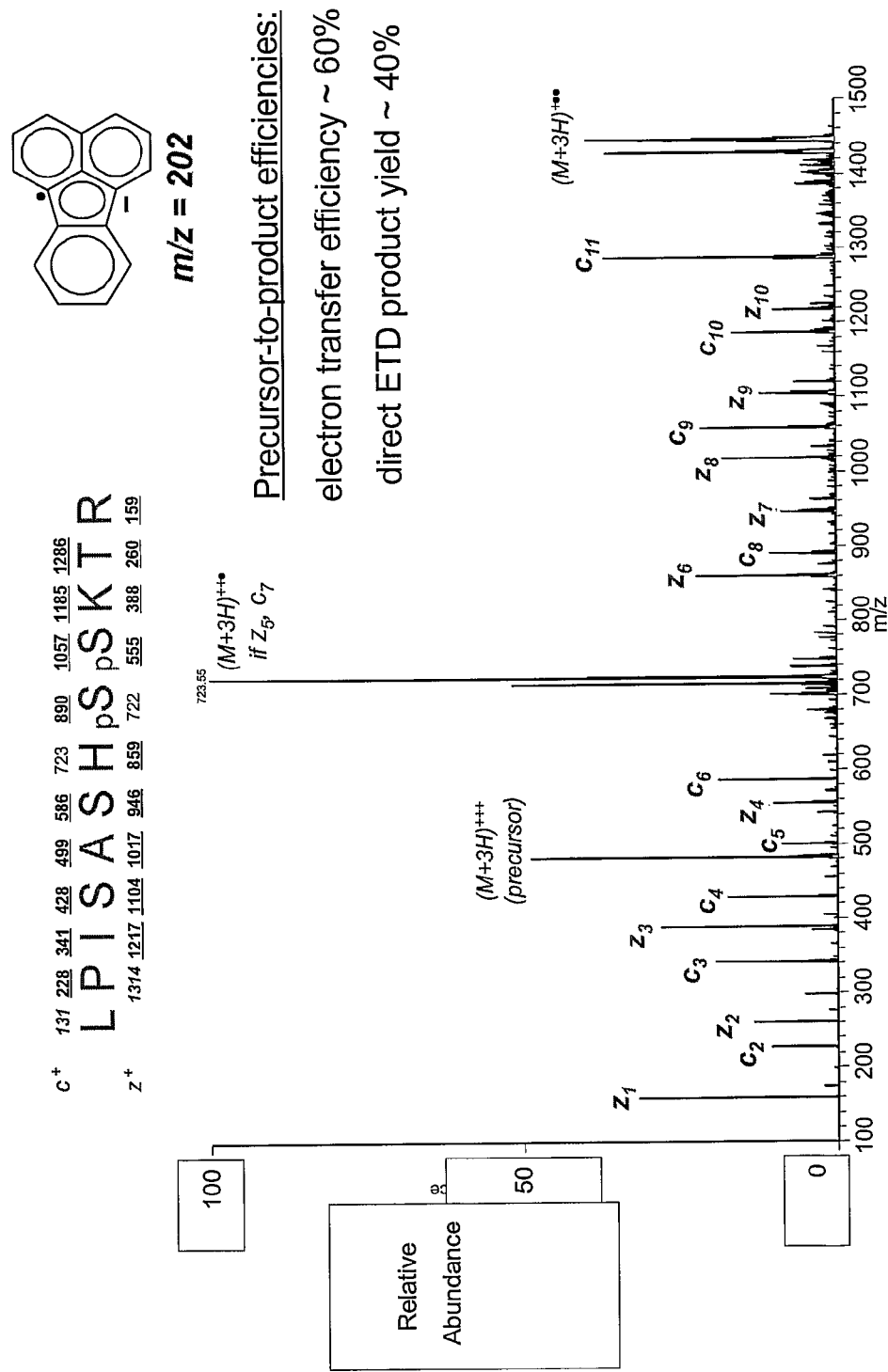
FIG. 9 represents a single-scan ETD-MS/MS spectrum resulting from the 50 ms reaction of m/z 202, from the radical anion of fluoranthene, with m/z 482 (triply-protonated phosphopeptide, LPISASHpSpSKTR; SEQ ID NO: 1).

FIG. 9 represents a single-scan ETD-MS/MS spectrum resulting from the 50 ms reaction of m/z 202, from the radical anion of fluoranthene, with m/z 482 (triply protonated phosphopeptide, LPISASHpSpSKTR; SEQ ID NO: 1). Here only products of electron transfer are observed. Of the observed products, two-thirds correspond to products of direct electron transfer dissociation. And approximately ⅓ of the products are the result of electron transfer without dissociation. These products can, however, be collisionally activated to generate products ions of type c and z (see section on low-energy activation). This indicates the initial electron transfer event induces dissociation of the peptide backbone; however, the precursor peptide ion can remain intact through other non-covalent interactions. On the other hand, the low-energy activation could actually trigger and ETD-like fragmentation pathway. In any event, the radical anion of fluoranthene induces electron transfer with high efficiency.

A plot of electron transfer dissociation efficiency vs. reaction q (q is a reduced parameter and affects ion motion, among other things, in the ion trap) was prepared. From this plot ~1300 counts (arbitrary units) are produced for products derived from electron transfer (q value~0.33). With no reaction the precursor intensity is ~3000 counts. We estimate with 100% electron transfer efficiency we would produce ~2000 counts (detector will produce ~⅔ the response for a +2 ion as compared to a +3). From this plot we estimate electron transfer efficiency to be 60%. Direct dissociation via electron transfer accounts for two-thirds of this value, or ~40%

All of the aromatic hydrocarbons tested here induced electron transfer, with varying degrees of efficiency. Based on these results, we propose other aromatic hydrocarbons, not tested here, will behave similarly. Therefore, aromatic hydrocarbon compounds, in general, represent a preferred class of electron transfer inducing compounds when reacted with multiply charged cations. Further, modification of these compounds to include atom(s) of sulfur, oxygen, or nitrogen (heterocyclics) should not alter their electron transfer capability and are therefore are to be included in this group electron transfer promoting compounds. The table presents the compound, molecular weight, and the observed m/z of its corresponding anion(s). Other tested compounds include: acridine; 2,2' dipyridyl; 2,2' biquinoline; 9-anthracenecarbonitrile; dibenzothiophene; 1,10'-phenanthroline; 9' anthracenecarbonitrile; and anthraquinone. Anions derived from all of these compounds induced electron transfer dissociation to some extent.

Example 4

The methods described herein can be used to characterize large polypeptides and whole proteins, using sequential ion/ion reactions and online chromatography with a benchtop linear ion trap mass spectrometer. In this example, eluting, multiply protonated peptides and proteins are first isolated and then reacted with the radical anion of fluoranthene for a relatively short duration (~10 ms, ETD). Following this reaction, and the expulsion of excess fluoranthene anions, the resulting product ions are reacted with even electron anions of benzoic acid (~100-200 ms). This second reaction (PTR) serves to both simplify the spectrum, making spectral interpretation much easier, and to convert the various c and z-type product ions into predominantly singly charged cations.

Materials and Methods

Instrument Modification and Operation. All experiments were performed with a commercial RF quadrupole linear ion trap (QLT), the Finnigan LTQ mass spectrometer (Thermo Electron Corp., San Jose, Calif., USA) equipped with either a modified factory nano-flow electrospray ionization (ESI) source (chromatography experiments) or a nanospray robot (Advion Biosciences, Ithaca, N.Y., USA, infusion). The LTQ was modified to accept a Finnigan 4500 chemical ionization source (Thermo Electron Corp., San Jose, Calif., USA) placed at the rear of the instrument (Syka, et al., (2004) P Natl Acad Sci USA 101, 9528-9533). A batch inlet was used to volatilize molecules of both fluoranthene and benzoic acid into the CI source, where an electron beam generated anions of both species. The instrument control software (ITCL) was modified to accommodate the following sequence following precursor ion selection (isolation width 4 m/z units) and storage: (1) anion injection (~2 ms); (2) fluoranthene anion isolation (m/z 202, 10 ms); (3) ion/ion reaction of anion and precursor cation (~10-15 ms); (4) removal of excess fluoranthene anions and storage of ETD products; (5) injection of anions (~2 ms); (6) application of selective waveform to remove m/z 202 and other background anion species (~5 ms); (7) ion/ion reaction of purified benzoic acid anions (m/z 121) with ETD product ions (~100-150 ms); (8) removal of excess benzoic acid anions and mass analysis of product ions.

Sample preparation. Histone H3.1 was isolated and separated from asynchronously growing HeLa cells, as previously described (Luger, et al., (1997) Nature 389, 251-260). A 5 μg-containing aliquot of histone H3.1 was digested with Glu-C (Roche, Palo Alto, Calif., USA) in 100 mM ammonium acetate (pH 4.0) at an enzyme-to-protein ratio of 1:15 for 4 hrs at 37° C. The resulting peptides were fractionated by HPLC; fractions containing the 1-50 residue were concentrated, resuspended in 100 mM ammonium bicarbonate (pH=8.5), and treated with an equal amount of propionylation reagent as described (Syka, et al., (2004) Journal of Proteome Research 3, 621-626). The reaction mixture was lyophilized to dryness and resuspended in 0.1% aqueous acetic acid. Histone H2A.Z was isolated from chicken erythrocytes as described in Dryhurst, D., Thambirajah, A. A. & Ausio, J. (2004) Biochemistry and Cell Biology-Biochimie Et Biologie Cellulaire 82, 490-497.

Chromatography. An Agilent 1100 Series binary HPLC system (Palo Alto, Calif., USA) was interfaced with the LTQ mass spectrometer for online protein/peptide separations. Approximately 100 fmol (each; from Sigma Aldrich, St. Louis, Mo., USA; unless noted) of vocative intestinal peptide, angiogenesis II, bovine ubiquitin, bovine cytochrome C, recombinant histone $H_2B$, bovine albumin (Upstate, Chicago, Ill., USA), and ~10 μmol H2A.Z mixture were pressure loaded onto a monolithic capillary column (360 μm×100 μm i.d., 5 cm column length, LC Packings, Sunnyvale, Calif., USA) equipped with a 30 μm SilicaTip™ ESI emitter (New Objective, Woburn, Mass., USA) and gradient eluted with a linear gradient of 0-60% B in 12 min and 60-100% B in 2 min (A=0.1M formic acid, B=70% acetonitrile in 0.1M formic acid, flow rate=1 μL/min).

Propionylated histone H3.1 (1-50 residue, 10 μmol) was pressure loaded onto a self-prepared nano-HPLC column (360 μm×50 μm i.d. fused silica packed with 7 cm of $C_{18}$ reversed-phase material (ODS-AQ, YMC, Waters, Milford, Mass., USA); equipped with an integrated, laser-pulled, ESI emitter. Peptides were eluted with a flow rate of 60 μL/min, using a linear gradient of 0-5% B in 15 min and 5-100% B in 15 min (A=0.1M acetic acid, B=70% acetonitrile in 0.1M acetic acid).

Results

Sequential ion/ion reactions. A 15 ms reaction of the +13 charge state of ubiquitin (8.5 kD, m/z 659, 76 residues) with radical anions of fluoranthene generates the tandem mass spectrum displayed in FIG. 10A. Several hundred highly charged, unresolved fragment ions are observed following this relatively short reaction. Theoretically these product ions possess charges (z) ranging from 1-12, recall the benchtop ion trap system used here can resolve z for $z \leqq 2$. And, with ~146 possible unique c and z-type fragments spread among numerous charge states—more or less confined within a 1000 m/z range—spectral interpretation, at this point, is simply not possible.

Figure 10:
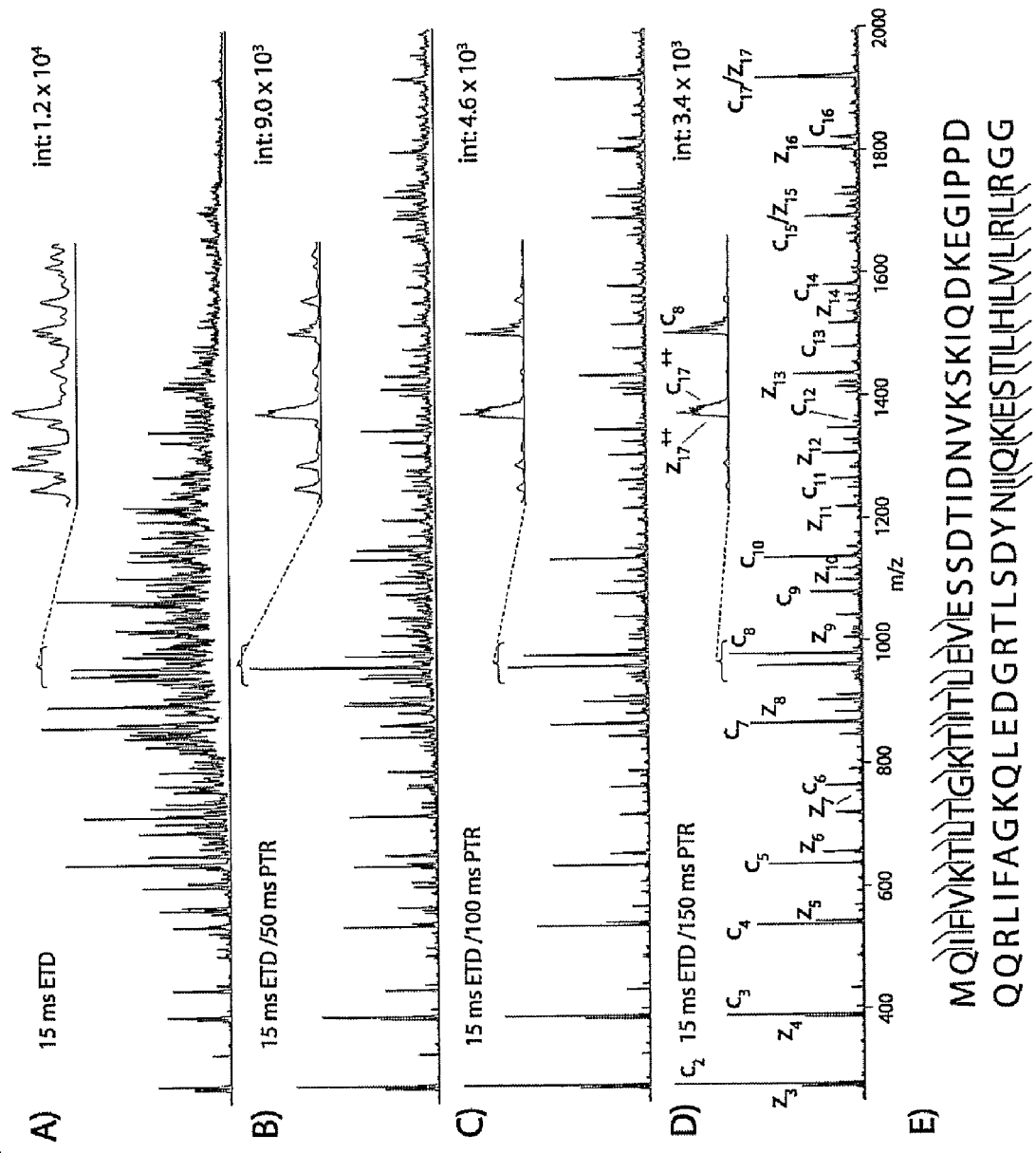
FIGS. 10A-10E represent data from tandem mass spectrum of ubiquitin generated by ion/ion reactions. Whole protein dissociation (ubiquitin +13, m/z 659) following a 15 ms reaction with the radical anion of fluoranthene (FIG. 10A). Note production of several hundred highly charged unresolved c and z-type fragment ions.
Figure 11:
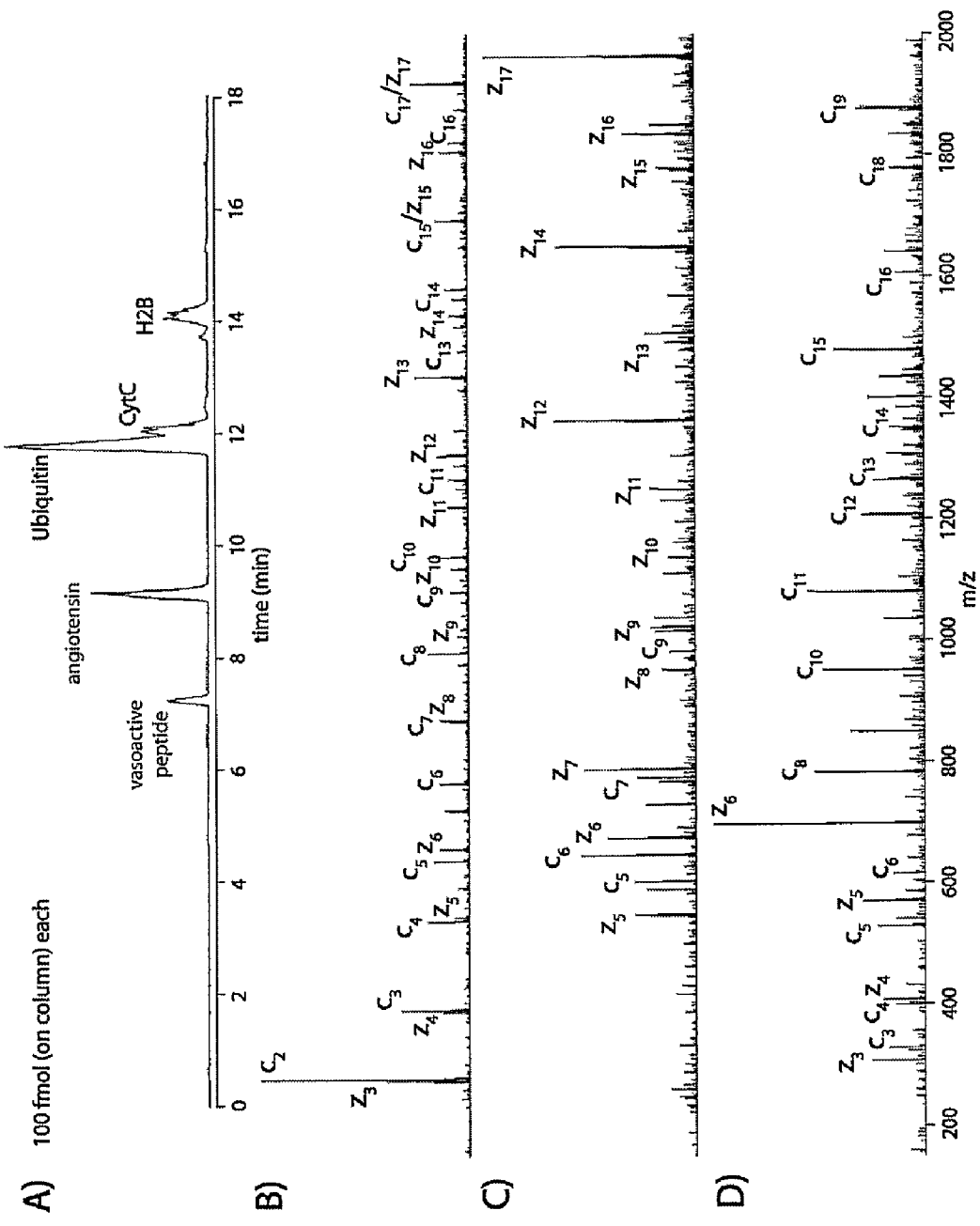
FIGS. 11A-11D represent tandem mass spectra of proteins in a mixture generated by a combination of on-line chromatography and sequential ion/ion reactions. Chromatographic separation of whole proteins with automated online sequential ion/ion reactions is shown in FIG. 11A.
Figure 12:
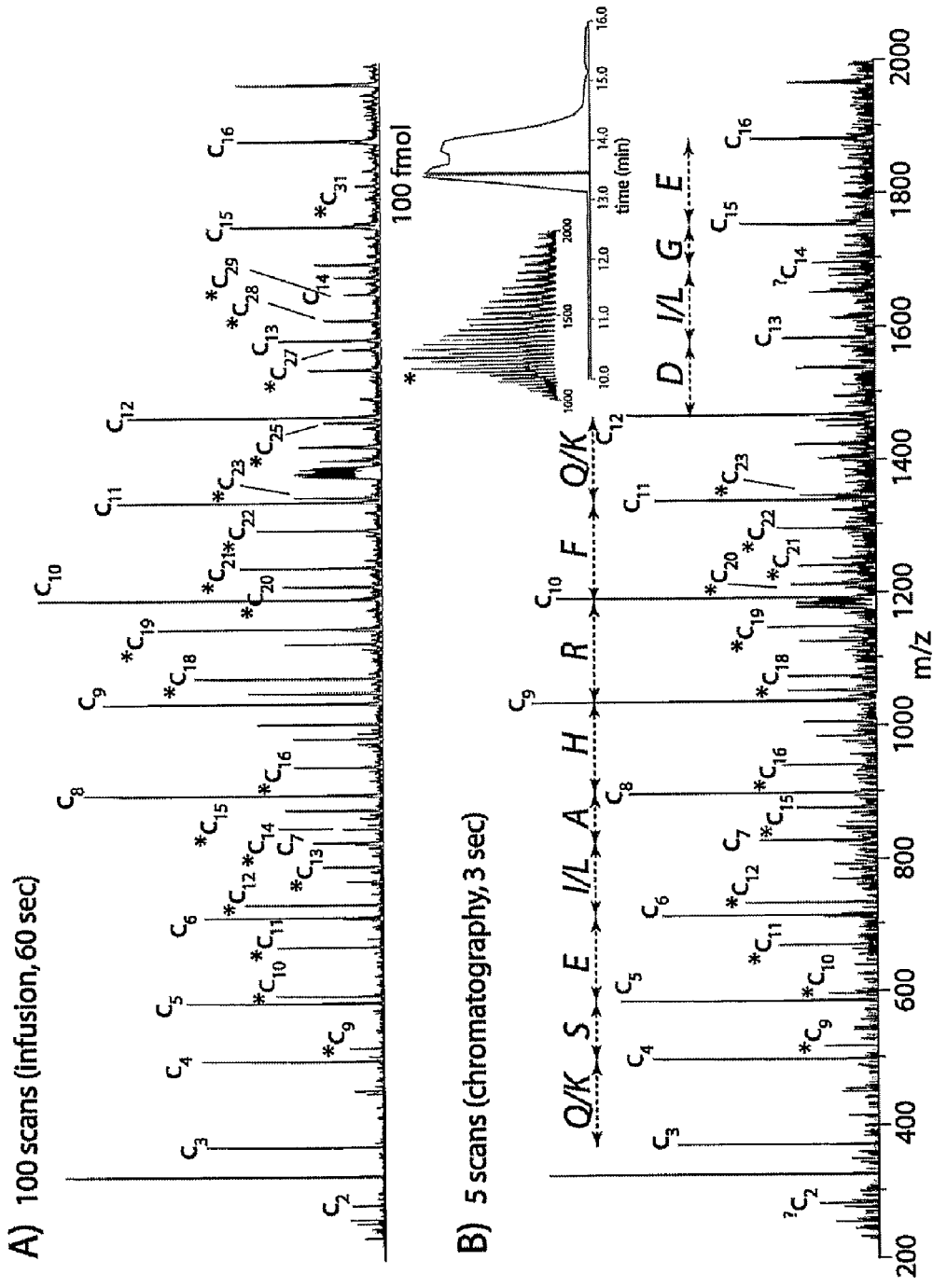
FIGS. 12A & 12B represent tandem mass spectra of albumin generated by sequential ion/ion reactions.

The mass spectrum (FIG. 10A), resulting from the initial ETD ion/ion reaction, can be simplified by sequestering the entire mixture of highly charged product ions, and reacting them with a second anion, deprotonated benzoic acid. This second reaction (PTR) removes excess charge from the diverse population of multiply charged fragment ions. Recall ion/ion reaction rates increase proportionally with charge squared; therefore, adjustment of the PTR reaction duration allows one to control the charge state of the resulting products. In this experiment multiple PTR reaction times were employed (50, 100, and 150 ms; FIGS. 10B, 10C, and 10D, respectively). As the reaction period is extended, the higher-charged fragments are preferentially concentrated to lower charge states—predominately singly charged products in the case of the 150 ms reaction (FIG. 10D). This effect can be observed by following the small expanded region of each spectrum plotted in FIG. 10. Mass analysis following the brief 15 ms ETD reaction produces several isobaric, highly charged fragments within the 60 m/z expanded range. Gradually these multiply protonated products are removed from the spectrum and after 150 ms only the three significant product ions remain: the doubly protonated $z_{17}$ and $c_{17}$, and singly charged $c_8$. Note while the doubly protonated signal of $c_{17}$ and $z_{17}$ is progressively degraded with increased reaction time, the singly protonated form (m/z 1919) increases proportionally.

From the spectrum displayed in FIG. 10D the entire amino and carboxy terminus of the protein can be sequenced by subtracting consecutive c and z-type product ion mass-to-charges within each respective series (17 residues deep from either end). The mass spectrometer used in these studies has an m/z range limited to 2000 which, of course, constrains the depth of observed coverage. Obviously higher mass c and z-type fragment ions are produced following the ETD reaction (FIG. 10A); however, the simplifying proton transfer reaction increases their m/z values beyond our mass range. Even with this limited m/z range coverage can be extended by identifying doubly protonated fragment ions, the upper limit of our resolving power (with the 100 ms PTR conditions we observe a population of doubly protonated fragment series that increases coverage to ~35 residues from either end).

Figure 2:
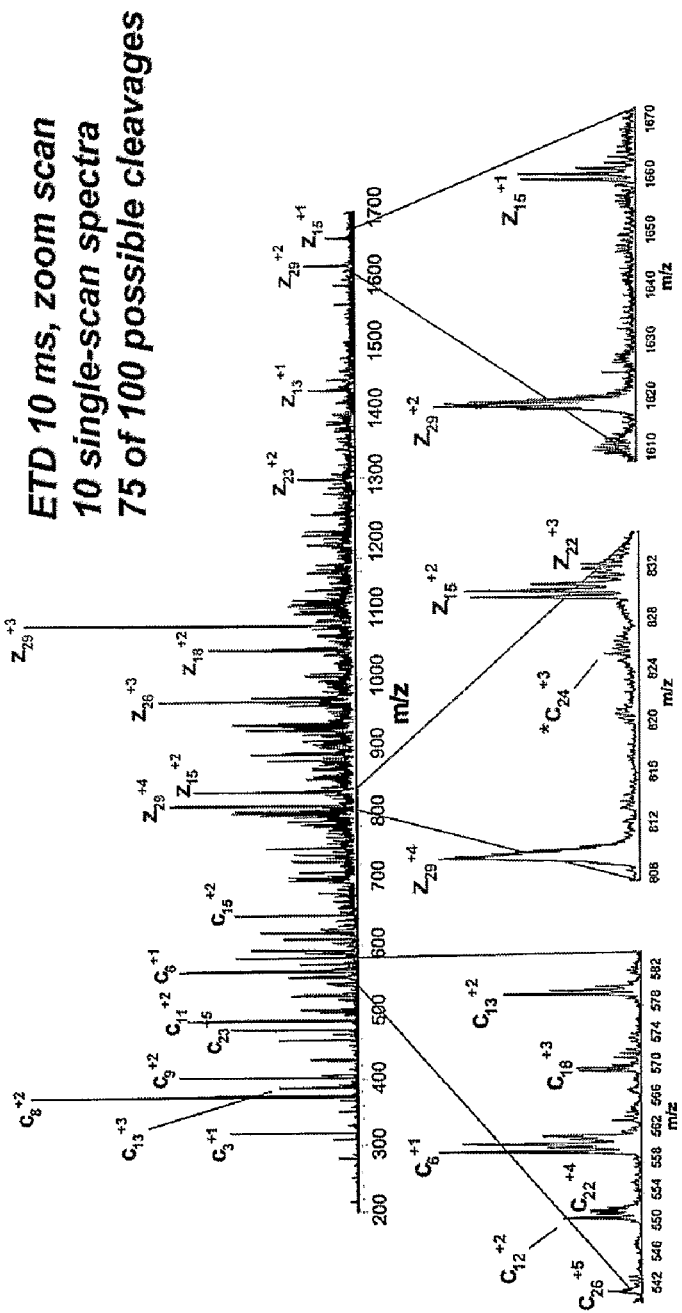
FIG. 2 represents a product ion spectrum obtained following a 15 ms reaction of the ETD-inducing anion, fluoranthene, with the +10 cation of residues 1-52 of histone H4 (SGRGKGGKGLGKGGAKRHRKVLRDNIQGITKPAI RRLARRGGVKRISGLIYE; SEQ ID NO: 2). Observed are hundreds of c and z-type fragment ions, many of which are multiply charged.

Whole protein sequencing with online chromatography. To demonstrate the viability of intact protein sequencing with online chromatography 100 fmol (each) of three proteins—ubiquitin, cytochrome C, and human histone H2B—were loaded onto a monolithic capillary column and gradient eluted into the mass spectrometer (FIG. 11A). Following a full m/z scan the two most abundant m/z ratios were selected for interrogation using sequential ion/ion reactions (15 ms ETD followed by 150 ms PTR, each spectrum the average of 4 single-scan spectra), this process was repetitively cycled throughout the course of the experiment. FIGS. 2B-D displays the tandem mass spectra generated following automated selection and interrogation of each eluting protein. Each spectrum, acquired in ~2 seconds, defines the amino and carboxy-terminus of the precursor protein (up to ~20 residues). Due to the heme group located on the amino terminus of cytochrome c, the c-type fragment series ceases at the ninth residue (likewise observed with ECD fragmentation).

Shown in FIG. 12A is the tandem mass spectrum of the $(M+49H)+^{49}$ ion of albumin (66 kDa, m/z 1381) generated using a combination of ETD (10 msec) and PTR (150 msec). This spectrum defines the first 31 amino acids at the N-terminus of the protein. These data were obtained by averaging 100 single scans acquired over 60 sec from an infused sample. No sequence ions, however, from the carboxy-terminus could be identified in the spectrum. Previous works have noted gas-phase protein conformation can affect the production, or at least, the observation of fragmentation following ECD, (as well as cross linking of the polymer by di-sulfide bridges etc). Even so, this result provides direct evidence that whole proteins of ordinary size (~66 kDa) are readily identified, without prior processing, on a benchtop mass spectrometer. To further assess the capabilities of the method 100 fmol of the protein was loaded on column and gradient eluted into the mass spectrometer under the same conditions described above. As the protein eluted, abundant charge-states were automatically isolated for direct analysis using the same sequential ion/ion reactions used in the infusion experiment. FIG. 12B displays one of the resulting mass spectra—the average of 5 single-scan spectra (~3 second acquisition). Here every singly charged c-type ion that was previously observed (during the infusion experiment) is readily distinguishable with sufficient signal/noise. Some of the higher m/z doubly protonated c-type ions are no longer discernable from the background; nonetheless, the spectrum clearly defines the first 23 residues of the intact protein.

Figure 13:
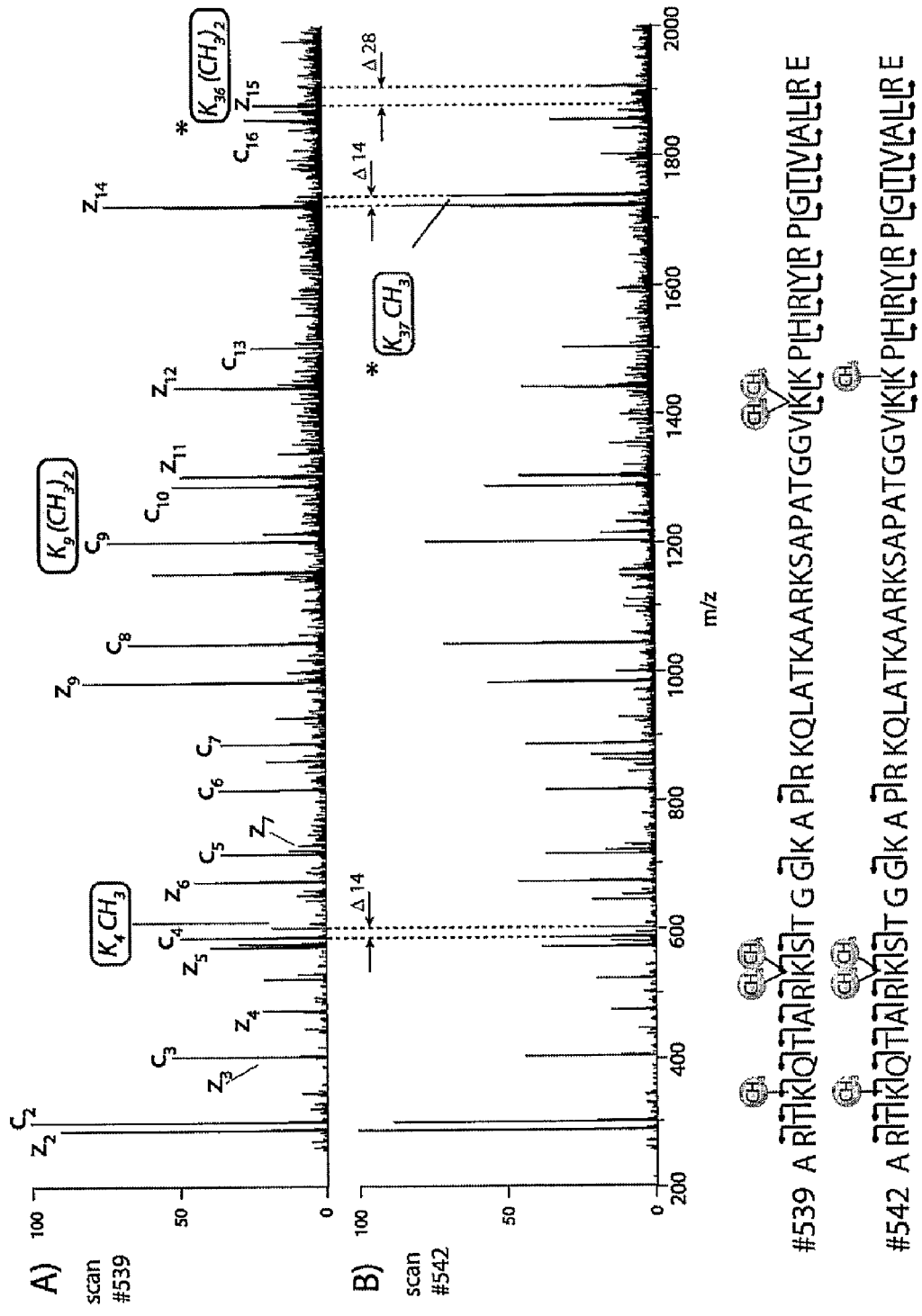
FIGS. 13A & 13B represents data from an online chromatographic separation of large peptides (ARTKQTARK-STGGKAPRKQLATKAARKSAPAT GGVKKPHRYRPGTVALRE; (SEQ ID NO: 6), representing residues 1-50, ~½ the protein) from histone H3.1 followed by automated sequential ion/ion reactions (ETD/PTR) and mass spectrometry.

Sequencing highly modified, large peptides. The N-terminal half of histone H3.1, a highly post-translationally modified region of the protein (residues 1-50, harvested from asynchronous human cells), was isolated and analyzed with a chromatographic separation coupled online to sequential ion/ion reactions and mass spectrometric analysis. The first scan (FIG. 13A, the average of 4 single-scan spectra, ~2 second acquisition) results from the automated interrogation—15 ms ETD followed by 150 ms PTR—of an early eluting peptide. A near-complete series of c-type ions (10 of 11) at the N-terminus demonstrates that $K_4$ and $K_9$ are modified with mono- and di-methyl groups, respectively. Analysis of the z-type ion series indicates the c-termini is not modified until $K_{36}$, which contains a dimethylated lysine. At this point, given the limited m/z range, the "center" portion of the peptide will remain uncharacterized. Still the present system can uncover global modification patterns that would otherwise remain obscured. For example, FIG. 13B displays a later eluting peptide (~6 seconds) contains a similar, but different, modification pattern. Inspection of the c-type ion series reveals the N-terminus of this peptide is modified identically to the previous species; however, an m/z shift in the higher-mass z-type ions confirm an unmodified $K_{36}$ residue followed by a monomethylated $K_{37}$. Note this later spectrum comprises fragment ions from both species (co-elution), e.g., the presence of two $z_{14}$ ions—one unmodified at $K_{37}$ (the earlier species, ~60%) and the $K_{37}$ monomethylated form (the later peptide, ~40%).

Figure 14:
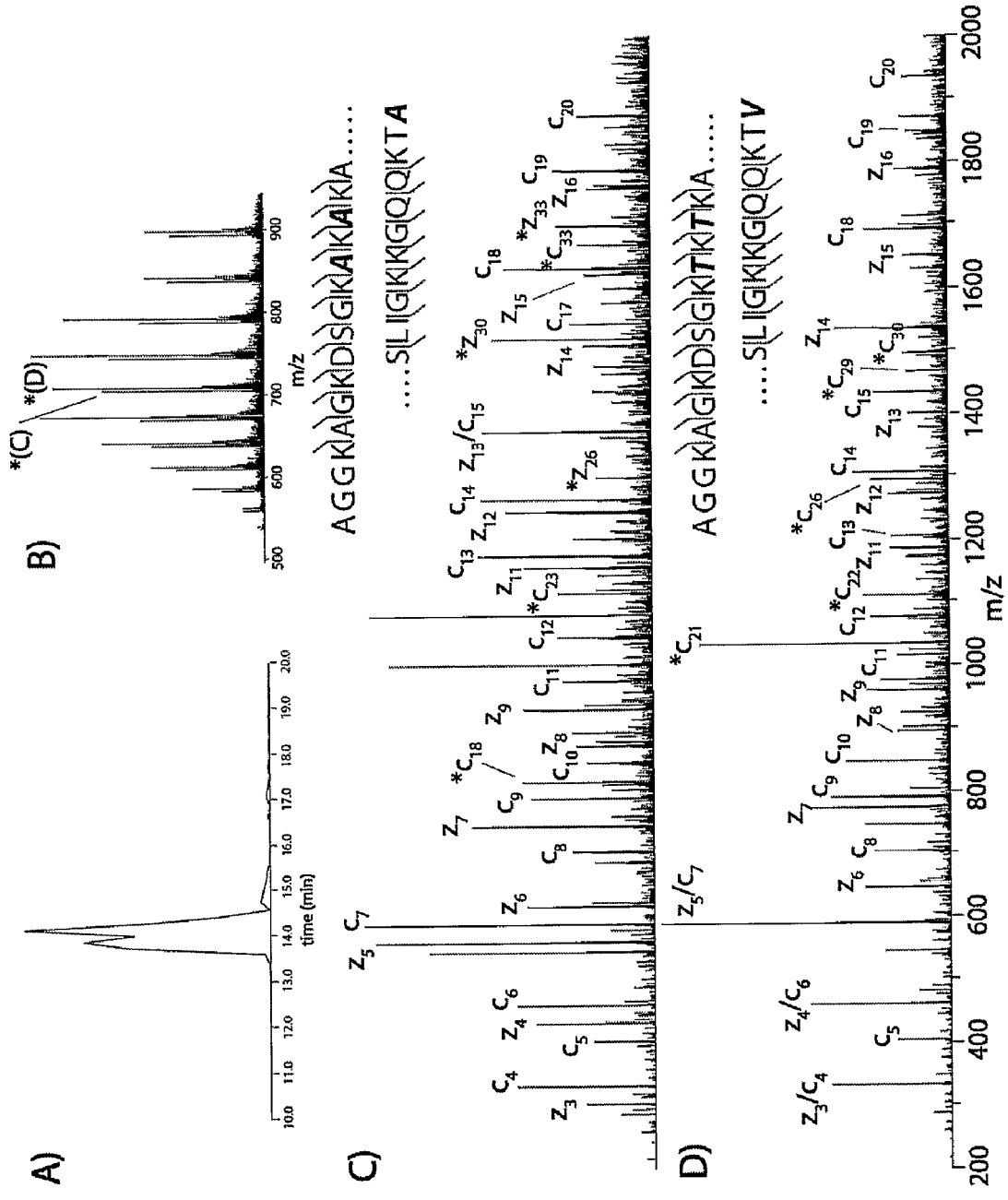
FIGS. 14A-14D provide sequence analysis of histone H2A.Z isoforms by on-line chromatography and sequential ion/ion reactions.

Sequencing protein mixtures. FIG. 14 displays results, following online chromatographic elution and sequential ion/ion reactions, for the intact analysis a wild-type protein mixture (chicken histone H2A.Z). The full m/z spectrum obtained for major eluting species indicates the presence of two distinct protein forms: $M_r$~13,380 and 13,456 Da, following deconvolution. The lighter protein, with a measured molecular weight of 13,380 Da, is within 2 Da of the unmodified, previously described chicken histone H2A.Z isoform. The heavier form, ~76 Da, was surmised to be probably due to PTM. Precursor m/z peaks were selected for further interrogation via sequential ion/ion reactions (15 ms ETD/150 ms PTR). The product ion spectrum of the lower molecular weight species identifies the protein as unmodified histone H2A.Z (consecutive c and z-type ions are observed to define the approximately the first 30 residues from either end of the protein, FIG. 14C). Inspection of the product ion spectrum for the heavier species, however, rules out the possibility of PTM; instead an m/z shift of 30 units at the twelfth and fourteenth residues of the amino terminus ($c_{12}$ and $c_{14}$), compared to the unmodified H2A.Z sequence, is observed. This indicates the alanine residues residing in positions 12 and 14 of H2A.Z have been substituted for threonine residues in the heavier protein. Another difference was found in the z-type ion series of the heavier protein—it is increased by 28 m/z units (FIG. 14D, though this discrepancy can only be located to the first three amino acids). Since the c-type ion series indicated 2 amino acid changes, the first 30 N-terminal amino acids, as interpreted from the dissociation spectrum (de novo), were subjected to a BLAST (basic local alignment search tool) search to identify any H2A.Z isoforms containing the detected amino acid changes.

Surprisingly, the search returned a protein having the exact N-terminal amino acid sequence, as identified by ETD/PTR, with threonine residues at position 12 and 14. This protein was termed 'hypothetical protein' from chicken and is not presently described as an H2A.Z variant. Comparison of the entire H2A.Z sequence with the 'hypothetical protein' sequence revealed a total of 4 amino acid changes: A12TA14TT38SA128V. The change of valine to alanine corresponds to a mass addition of 28 Da and explains the 28 Da increase of the z-type ion series of the heavier protein. The total net change of 74 Da, due to those 4 changed amino acids, is in agreement with the molecular weight determined by the full m/z scan (~76 Da). Further confirmation that the isolated protein contained the above amino acid changes was obtained by sequencing peptides in a Glu-C digest using tandem mass spectrometry (ETD/PTR).

Discussion.

Ion-ion chemistry. Ion/ion reaction duration is an important parameter that remains, as yet, unoptimized. For example, in these experiments the ETD reaction period was kept low to minimize multiple electron transfer events—consecutive electron transfer can result in the production of internal fragments. For example, a $c_{50}$ fragment, produced following a single electron transfer to the whole protein cation, could subsequently receive an electron, cleave, and form two product ions—e.g., $c_{25}$ and $z'_{25}$. Of course, the N-terminal fragment, $c_{25}$, is still recognizable within the context of the original precursor protein; however, the $z'_{25}$ product contains neither the amino nor carboxy-terminus of the original precursor and thus appears, with a variety of other similar products, as elevated noise. Besides increasing chemical noise, multiple electron transfer events can also serve to generate a disproportionate amount of low m/z c and z-type fragment ions.

PTR reaction duration is also ideally adjusted to coincide with the charge and size of the precursor protein. Future implementations of this methodology will doubtless contain the ability to automatically prescreen precursor ion charge state (obtain charge and MW) using PTR. With this information the optimal ETD and PTR reaction period will be calculated and employed in the subsequent ion/ion reaction series. Depending on the determined m/z, the PTR time could be adjusted so as to reduce the entire c and z-type ion series to the single charge state (large protein) or to shorten the reaction period to leave both singly and doubly charged species and increase sequence coverage (large peptide/small protein).

Instrumentation. Future enhancements of this ion/ion technology will almost certainly come in the form of instrumentation. For example, multi-segmented ion traps that allow fully independent anion and cation isolations will reduce acquisition time and enhance anion purity. Higher-capacity devices will allow increased ion storage and, thus, will decrease the need for spectral averaging (at present, we start with ~2-5 times the number of precursor ions used for a conventional CAD experiment). Finally, hybridization of the device with other mass analyzers (e.g., FT-ICR-MS, TOF-MS, etc.) will be of obvious utility for increasing mass accuracy, mass resolution, and/or m/z range.

Data analysis. Translation of tandem mass spectra to peptide/protein sequence is usually accomplished with a protein database searching algorithm, e.g., SEQUEST (Eng, et al., (1994) Journal of the American Society for Mass Spectrometry 5, 976-989). These search algorithms were designed especially for the type of fragmentation achieved with CAD—fragmentation that is highly dependent on which amino acids are present, their order, and the presence of PTMs. Neutral losses of amino acid side-chains or PTMs is common. With all these caveats, direct interpretation (by computer, de novo sequencing) of CAD tandem mass spectra (peptide or whole protein) remains challenging. In contrast, ETD does not suffer from these limitations; rather, peptide backbone fragmentation occurs randomly to generate a homologous series of c- and z-type fragment ions. For example, note the consecutive c-type ion series in FIG. 13B that allows direct "reading" of the protein's amino-terminus. This predictability should make possible automated de novo sequencing, which, in turn, may eliminate the reliance on protein database searching. ETD/PTR-derived tandem mass spectra, from whole proteins, could be analyzed in the following manner: (1) preprocessing via a de novo algorithm to generate sequence tags from the present c and z-type ion series, (2) calculated amino acid sequences searched via a BLAST (basic local alignment search tool) alignment of a genomic database, and (3) all possible sequence-containing proteins (identified in step 2) are fragmented in silico with subsequent spectral alignment and comparison with the measured protein intact MW.

The sequential ion/ion reactions described herein allow rapid sequence analysis of intact proteins on low-cost, benchtop ion trap mass spectrometers. As demonstrated, each spectrum contains a series of c-type ions—characteristic of the amino acid sequence of the amino-terminus of the protein—and a series of z-type ions to define the carboxy-terminus. Beyond that, the protein charge envelope (obtained in the full m/z spectrum) allows determination of the intact MW of each protein from which the N/C-terminal amino acids have been characterized. This will be used either to confirm the protein identity or to suggest the presence of PTMs or mutations in the molecule. Alternatively, discrepancies, from the predicted sequence, in either the intact MW or the N/C-terminal amino acid sequence can identify mRNA alternative splicing. Finally, besides proteomics applications, this technology should be particularly valuable for characterization of recombinant proteins, including truncated isoforms, employed as drugs or diagnostics in the biotechnology/pharmaceutical industry.

The invention claimed is:

1. A method of determining amino and carboxy terminal amino acid sequences of a polypeptide, said method comprising
introducing said polypeptide into an RF electric field ion containment device, wherein the polypeptide is in a multiply charged cationic state;
introducing gas-phase electron transfer reagent anions into said ion containment device; and
mixing the introduced electron transfer reagent anions, or derivative electron transfer reagent ions thereof, and the polypeptide, so as to facilitate electron transfer from the electron transfer reagent anions, or derivative electron transfer reagent ions thereof, to the polypeptide, to produce dissociation product cations;
introducing gas-phase proton accepting reagent anions into said ion containment device; and
mixing the introduced proton accepting reagent anions, or derivative proton accepting reagent ions thereof, and the dissociation product cations, so as to facilitate proton transfer from said dissociation product cations to the proton accepting reagent anions, or derivative proton accepting reagent ions thereof, to reduce the charge on the multiply charged dissociation product cations so the remaining charged c and z-type fragments consist essentially of fragments having four or fewer unit charges, wherein said derivative electron transfer reagent ions and said derivative proton accepting reagent ions are generated within said ion containment device during performance of said method;
mass (m/z) analyzing said remaining charged fragments; and
determining amino and carboxy sequences of the polypeptide.

2. The method of claim 1 further comprising the step of removing the electron transfer reagent anions, and electron transfer derivative reagent ions thereof, prior to the introduction gas-phase proton accepting reagent anions.

3. The method of claim 1 wherein the polypeptide has a mass of at least 5000 Daltons.

4. The method of claim 1 wherein the polypeptide has a mass of at least 10,000 Daltons.

5. The method of claim 1 wherein said remaining charged c and z-type fragments consist essentially of fragments having three or fewer unit charges.

6. The method of claim 1 wherein said remaining charged c and z-type fragments consist essentially of fragments having two or fewer unit charges.

7. The method of claim 1 wherein said remaining charged c and z-type fragment ions consist essentially of singly charged fragments.

8. The method of claim 1 wherein said step of mass (m/z) analyzing the low charged fragments is performed with an RF ion trap mass (m/z) analyzer.

9. The method of claim 8 wherein said RF ion trap mass (m/z) analyzer is a 3D RF ion trap analyzer.

10. The method of claim 7 where said RF ion trap mass (m/z) analyzer is a linear ion trap analyzer.

11. The method of claim 1 where said step of mass (m/z) analyzing the low charged fragments is performed with a Fourier Transform ion cyclotron resonance (FTICR) mass (m/z) analyzer.

12. The method of claim 1 where said step of mass (m/z) analyzing the low charged fragments is performed with a time-of-flight mass (m/z) analyzer.

13. The method of claim 1 where said step of mass (m/z) analyzing the low charged fragments is performed with an orbitrap mass (m/z) analyzer.

14. The method of claim 1 further comprising the step of determining the molecular weight of the intact polypeptide by mass spectrometric analysis.

15. The method of claim 1 wherein the radical gas-phase electron transfer anions are radical gas-phase anions generated from a polyaromatic hydrocarbon or substituted polyaromatic hydrocarbon compounds.

16. The method of claim 15 wherein the gas-phase electron transfer anion is generated from a low electron affinity substrate selected from the group consisting of anthracene, 9,10 diphenyl-anthracene, napthalene, fluorene, phenanthrene, pyrene, fluoranthene, chrysene, triphenylene, perylene, acridine; 2,2' dipyridyl; 2,2' biquinoline; 9-anthracenecarbonitrile; dibenzothiophene; 1,10'-phenanthroline; 9' anthracenecarbonitrile; and anthraquinone.

17. The method of claim 1 wherein the proton accepting reagent anion is derived from a compound selected from the group consisting of a carboxylic acid, phenolic, and alkoxide containing compound.

18. The method of claim 1 wherein the proton accepting reagent anion is an anion of a compound selected from the group consisting of benzoic acid, perfluoro-1,3-dimethylcyclohexane, sulfur hexafluoride, and perfluorotributylamine.

19. The method of claim 1 wherein the intact polypeptide is ionized by electrospray ionization prior to mixing the polypeptide with the gas-phase electron transfer anion.

20. The method of claim 10 where anions are injected along the linear axis of the RF linear multipole ion trap.

21. The method of claim 1 further comprising the steps of
expelling the remaining anions from the RF ion trap, while retaining the electron transfer product cations within the linear ion trap; and
subjecting the electron transfer product ions to a low-energy, off-resonance kinetic excitation to effect collisional activation that produces less than 20% conventional collision-activated dissociation products prior to the step of introducing gas-phase proton accepting reagent anions into said ion containment device.

22. The method of claim 21 wherein the low-energy activation comprises off-resonance kinetic excitation.

23. A method of determining amino and carboxy terminal amino acid sequences of a polypeptide, said method comprising introducing said polypeptide into an RF electric field ion containment device, wherein the polypeptide is in a multiply charged anionic state;

introducing gas-phase electron transfer reagent cations into said ion containment device; and mixing the gas-phase ions and the ionized polypeptide so as to facilitate electron transfer from the anion to the cations, and thus inducing the production of negative electron transfer dissociation product ions;

introducing gas-phase proton donor reagent cations into said ion containment device;

mixing the introduced proton donor reagent cations, or derivative proton donor reagent cations thereof, and the dissociation product anions, so as to facilitate proton transfer to said dissociation product anions from the proton donor reagent cations, or derivative proton donor reagent cations thereof, to reduce the charge on the multiply charged dissociation product cations so the remaining charged c and z-type fragments consist essentially of fragments having four or fewer unit charges, wherein said derivative electron transfer reagent ions and said derivative proton accepting reagent ions are generated within said ion containment device during performance of said method;

mass (m/z) analyzing said remaining charged fragments; and determining amino and carboxy sequences of the polypeptide.

* * * * *